US008877179B2

(12) United States Patent
Mercenier et al.

(10) Patent No.: US 8,877,179 B2
(45) Date of Patent: Nov. 4, 2014

(54) FROZEN CONFECTIONS CONTAINING PROBIOTIC MICRO-ORGANISMS

(75) Inventors: Annick Mercenier, Bussigny (CH); Guenolee Prioult, Bern (CH); Sophie Nutten, Palezieux-Village (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/884,547

(22) PCT Filed: Nov. 11, 2011

(86) PCT No.: PCT/EP2011/069924
§ 371 (c)(1),
(2), (4) Date: May 9, 2013

(87) PCT Pub. No.: WO2012/062900
PCT Pub. Date: May 18, 2012

(65) Prior Publication Data
US 2013/0236581 A1 Sep. 12, 2013

(30) Foreign Application Priority Data

Nov. 11, 2010 (EP) .................................. 101900889

(51) Int. Cl.
| A01N 63/00 | (2006.01) |
| A23L 1/28 | (2006.01) |
| A23C 9/12 | (2006.01) |
| A61K 35/74 | (2006.01) |
| A23L 1/30 | (2006.01) |
| A23L 1/308 | (2006.01) |
| A23G 9/36 | (2006.01) |
| A23C 9/123 | (2006.01) |

(52) U.S. Cl.
CPC .............. *A61K 35/741* (2013.01); *A61K 35/744* (2013.01); *A23L 1/3014* (2013.01); *A23L 1/308* (2013.01); *A23Y 2220/73* (2013.01); *A23V 2200/30* (2013.01); *A23Y 2220/43* (2013.01); *A61K 35/745* (2013.01); *A23V 2002/00* (2013.01); *A23G 9/36* (2013.01); *A23C 2260/152* (2013.01); *A61K 35/747* (2013.01); *A23C 9/1234* (2013.01); *A23Y 2220/49* (2013.01); *A23Y 2300/55* (2013.01); *A23G 9/363* (2013.01); *A23Y 2280/51* (2013.01)
USPC ......... 424/93.4; 424/93.3; 424/93.45; 426/61

(58) Field of Classification Search
CPC ........... A23V 2002/00; A23V 2200/30; A23V 2200/3202; A23V 2200/3204; A23V 2250/064; A23C 2260/152; A23C 9/1234; A23G 9/32; A23G 9/327; A23G 9/36; A23G 9/363; A23L 1/035; A23L 1/3014; A23L 1/308; A23Y 2220/43; A23Y 2220/49; A23Y 2220/73; A23Y 2280/51; A23Y 2300/55; A47F 1/08; A47F 1/12; A47F 3/02; A47F 5/02; A47F 5/05; A47F 5/06; A61K 35/741; A61K 35/744; A61K 35/745; A61K 35/747

See application file for complete search history.

(56) References Cited

U.S. PATENT DOCUMENTS

| 5,308,628 | A | 5/1994 | Schol et al. | |
| 7,572,473 | B2 * | 8/2009 | Gutknecht et al. | ............. 426/582 |
| 2002/0015756 | A1 | 2/2002 | Gutkevich | |
| 2002/0028269 | A1 | 3/2002 | Verrips | |
| 2003/0008016 | A1 * | 1/2003 | Crum et al. | .................... 424/535 |
| 2003/0031758 | A1 * | 2/2003 | Koss et al. | ....................... 426/72 |
| 2003/0170217 | A1 | 9/2003 | Collins et al. | |
| 2004/0047896 | A1 * | 3/2004 | Malnoe et al. | ................ 424/439 |
| 2004/0197277 | A1 * | 10/2004 | Gonzales | ........................ 424/48 |
| 2005/0037110 | A1 | 2/2005 | Windhab et al. | |
| 2005/0180962 | A1 * | 8/2005 | Raz et al. | .................... 424/93.45 |
| 2006/0002908 | A1 | 1/2006 | Collins et al. | |
| 2008/0026104 | A1 | 1/2008 | Turan et al. | |
| 2008/0206212 | A1 | 8/2008 | McMahon et al. | |
| 2008/0206213 | A1 | 8/2008 | Herz et al. | |
| 2009/0035288 | A1 * | 2/2009 | Albers et al. | ............... 424/93.45 |
| 2009/0226418 | A1 | 9/2009 | Frenken et al. | |

FOREIGN PATENT DOCUMENTS

| CN | 1338940 | 3/2002 |
| CN | 1436046 | 8/2003 |
| CN | 101112218 | 1/2008 |
| CN | 101360512 | 2/2009 |
| CN | 101374425 | 2/2009 |
| CN | 101636172 | 1/2010 |
| EP | 0122105 | 10/1984 |
| EP | 2143784 | 1/2010 |
| WO | WO0042429 | 7/2000 |
| WO | WO0195741 | 12/2001 |
| WO | WO2005053416 | 6/2005 |
| WO | WO2007009568 | 1/2007 |
| WO | WO2009151330 | * 12/2009 |
| WO | WO2010000776 | * 1/2010 |

OTHER PUBLICATIONS

Di et al.—Journal of Dairy Science—Oct. 2010—2 pages.
T. Sashihara et al., "An Analysis of the Effectiveness of Heat-Killed Lactic Acid Bacteria in Alleviating Allergic Diseases", J. Dairy Sci 89:2845-2855—XP002512655, 2006.
Marshall et al., "Composition and Properties", Jan. 1, 2000—pp. 22-23, 28—XP002282748.
Christiansen et al., "Some properties of ice cream containing *Bifidobacterium bifidum* and *Lactabacillus acidophilus*", Muchwissenschaft 51 (9) 1998 XP000632258.

(Continued)

*Primary Examiner* — Chris R Tate
*Assistant Examiner* — Douglas F White
(74) *Attorney, Agent, or Firm* — K&L Gates LLP

(57) ABSTRACT

The present invention relates to the field of frozen yoghurt. In particular, the present invention provides frozen yoghurt compositions comprising non-replicating probiotic micro-organisms. These non-replicating probiotic micro-organisms may bioactive heat treated probiotic micro-organisms, for example. The present inventions also relates to health benefits provided by these non-replicating probiotic micro-organisms.

15 Claims, 18 Drawing Sheets

(56) References Cited

OTHER PUBLICATIONS

Vrese, Probiotika—eine Option fur die Sub-warenindustrie?, XP000656503, 1997.
Ouwehand et al., "The Health Effects of Cultured Milk Products with Viable and Non-viable Bacteria", International Dairy Journal, vol. 8, No. 9, Jan. 1, 1998, pp. 749-758 XP000952256.
C. Adams, "The probiotic paradox: live and dead cells are biological response modifiers," Nutr. Res. Rev., vol. 23, No., Jun. 2010, abstract only, 1 page.
Gibson et al. "Prebiotics: Development & Application" Copyright 2006, John Wiley & Sons, Ltd., 50 pages.
Chinese Office Action for Application No. 201180054393.9 dated Aug. 5, 2014, 17 pages.

* cited by examiner

OR

FROZEN CONFECTIONS CONTAINING PROBIOTIC MICRO-ORGANISMS

CROSS REFERENCE TO RELATED APPLICATIONS

The present application is a National Stage of International Application No. PCT/EP2011/069924, filed on Nov. 11, 2011, which claims priority to European Patent Application No. 10190889.5, filed Nov. 11, 2010, the entire contents of which are being incorporated herein by reference.

The present invention relates to the field of frozen yoghurt. In particular, the present invention provides frozen yoghurt compositions comprising non-replicating probiotic micro-organisms. These non-replicating probiotic micro-organisms may be bioactive heat treated probiotic micro-organisms or yet bioactive low temperature extruded probiotic micro-organisms, for example. The present inventions also relates to health benefits provided by these non-replicating probiotic micro-organisms.

The health benefits of probiotics are meanwhile well accepted in the art and were summarized, e.g., by Blum et al. in Curr Issues Intest Microbiol. 2003 Sep.; 4(2):53-60. Oftentimes probiotics are administered together with prebiotics in symbiotic formulations which may even have enhanced health benefits.

Usually, probiotics are sold today in the framework of yoghurt and yoghurt drinks, for example.

Probiotics can however only deliver their health effects if they are actually consumed by consumers. In other words, providing probiotics in products that are generally well liked will make the health benefits of probiotics accessible to a broad range of consumers. Frozen yoghurt is such a product that is well liked by almost everyone, in particular by children and teenagers. Frozen yoghurt is additionally generally seen as a low-calorie alternative to ice cream.

For ice cream M. W. Modler et al. report that an ice cream containing bifidobacteria and fructooligosaccharides is of remarkable interest to human health (Cult. Dairy Prod. J., 25, p. 4-9, 1990; Canadian Dairy, 75, p. 10, 1996). Likewise, EP307523 (Yakult Honsha KK) reports that a fermented milk containing prebiotic fibers may be packaged in the form of an ice cream and thus be used to treat certain gastrointestinal disorders.

Using this concept for frozen yoghurt would allow to extend this principle to frozen yoghurts.

However, bringing the dietary fibers into contact with the lactic acid bacteria has significant disadvantages. These disadvantages are of various types, and relate in particular to the premature destruction of the fibers during the preparation and storage of the dessert, and to the poor conditions in vivo in which the biological activity of these fibers develops, for example.

U.S. Pat. No. 6,399,124 aims to overcome these disadvantages by separating dietary fibers and probiotics in a frozen dessert by providing an edible barrier between a fiber containing support and a probiotic containing ice cream.

The probiotic bacteria are known to be capable of adhering to human intestinal cells and of excluding pathogenic bacteria on human intestinal cells. To have this activity, the probiotic bacteria must remain viable in the product until it is consumed. This is a challenge for industry and, for example, U.S. Pat. No. 4,308,287 suggests a method to accomplish this.

It would be desirable to have available a frozen yoghurt composition that is able to deliver probiotic benefits even after longer storage times under critical conditions for the probiotics, while being simple to prepare. It would be preferred if this was achieved by using natural ingredients that are safe to administer without side effects and that are easy to incorporate into frozen yoghurt compositions using state of the art industrial techniques.

It would also be desirable to further improve the immune boosting effect of probiotics in such preparations.

It would further be desirable to further improve the anti-inflammatory effect of probiotics in such preparations.

The present inventors have addressed this need. It was hence the objective of the present invention to improve the state of the art and to provide frozen yoghurt compositions that satisfy the needs expressed above.

The present inventors were surprised to see that they could achieve this object by the subject matter of the independent claim. The dependant claims further develop the idea of the present invention.

Accordingly, the present inventors propose to provide a frozen yoghurt composition comprising non-replicating probiotic micro-organisms.

Frozen yoghurts are frozen dairy products made from, or containing yogurt. Frozen yoghurts may be served as dessert or snack, for example.

The present inventors were able to show that even non-replicating probiotics can provide the health benefits of probiotics and may even have improved benefits.

Hence, the complicated measures to keep probiotics alive in the final product and to make sure that they arrive alive in the intestine seem to be unnecessary. Further, using non-replicating probiotics in a frozen yoghurt product also allows it to have probiotics and prebiotics together in one preparation without the risk of having unwanted premature destruction of the fibers during the preparation and storage of the product.

The amount of non-replicating micro-organisms in the ice cream composition of the present invention may correspond to about $10^6$ to $10^{12}$ cfu per serving.

Obviously, non-replicating micro-organisms do not form colonies, consequently, this term is to be understood as the amount of non replicating micro-organisms that is obtained from $10^4$ and $10^{12}$ cfu/g replicating bacteria. This includes micro-organisms that are inactivated, non-viable or dead or present as fragments such as DNA or cell wall or cytoplasmic compounds. In other words, the quantity of micro-organisms which the composition contains is expressed in terms of the colony forming ability (cfu) of that quantity of micro-organisms as if all the micro-organisms were alive irrespective of whether they are, in fact, non replicating, such as inactivated or dead, fragmented or a mixture of any or all of these states.

Any frozen yoghurt composition can be used for the purposes of the present invention. Examples are normal frozen yoghurts, low-fat frozen yoghurts, frozen yoghurts with no added sugar, or low-fat frozen yoghurts with no added sugar.

For example, such frozen yoghurt composition may comprise about 0-12 weight-% fat, about 5-15 weight-% non fat milk solids, about 5-32 weight-% carbohydrates, about 1-5 weight-% proteins and a total solid content of about 30-45 weight-%.

Of course, fruits, chocolate, vanilla, caramel, coffee, nuts, cereals, honey and or other flavour components may be added.

The frozen yoghurt composition may further comprise about 1-25 weight-% added sugar.

The frozen yoghurt may also comprise prebiotics.

"Prebiotic" means food substances that promote the growth of probiotics in the intestines. They are not broken down in the stomach and/or upper intestine or absorbed in the GI tract of the person ingesting them, but they are fermented by the gastrointestinal microflora and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412.

The prebiotics that may be used in accordance with the present inventions are not particularly limited and include all food substances that promote the growth of probiotics in the intestines. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides (FOS), galacto-oligosaccharides (IOS), isomalto-oligosaccharides, xylo-oligosaccharides, oligosaccharides of soy, glycosylsucrose (GS), lactosucrose (LS), lactulose (LA), palatinose-oligosaccharides (PAO), malto-oligosaccharides (MOS), gums and/or hydrolysates thereof, pectins and/or hydrolysates thereof.

Typical examples of prebiotics are oligofructose and inulin.

The frozen yoghurt composition in accordance with the present invention may further comprising an edible support associated with the frozen yoghurt, the support being edible by humans and comprising prebiotics.

These prebiotics may be of a protein or saccharide nature, chosen, for example, from vegetable pectins, chito-, fructo-, gentio-, galacto-, isomalto-, manno- or xylo-oligosaccharides, or soya bean, Polymnia sonchifolia, artichoke, onion or asparagus oligosaccharides, or resistant starches, or products high in [beta]-glucans such as an oats concentrate, for example (Playne et al.; Fukai et al., Soil Sci. Plant Nutr., 39, 567-571, 1993).

The preferred pectins are polymers of [alpha]-1,4-D-galacturonic acid having a molecular weight of the order of 10 to 400 kDa, which can be purified from carrots or tomatoes, for example (JP60164432). The preferred galacto-oligosaccharides comprise a saccharide part consisting of 2 to 5 repeating units of structure {-[alpha]-D-Glu-(1->4)-[beta]-D-Gal-(1->6)-} (Yakult Honsa Co., Japan). The preferred fructooligosaccharides are inulin-oligofructoses extracted from chicory which may comprise, for example, 1-9 repeating units of structure {-[beta]-D-Fru-(1->2)-[beta]-D-Fru-(1->2)-} (WO94/12541; Raffinerie Tirlemontoise S.A., Belgium), or oligosaccharides synthesized from sucrose units which may comprise, for example, a sucrose part consisting of 2 to 9 repeating units of structure {-[alpha]-D-Glu-(1->2)-[beta]-D-Fru-(1->2)-} (Meiji Seika Kasiha Co., Japan). The preferred maltooligosaccharides comprise a saccharide part consisting of 2 to 7 repeating units of structure {-[alpha]-D-Gal-(1->4)-} (Nihon Shokuhin Kako Co., Japan). The preferred isomaltoses comprise a saccharide part consisting of 2 to 6 repeating units of structure {-[alpha]-D-Glu-(1->6)-} (Showa Sangyo Co., Japan). The preferred gentiooligosaccharides comprise a saccharide part consisting of 2 to 5 repeating units of structure {-[beta]-D-Glu-(1->6)-} (Nihon Shokuhin Kako Co., Japan). Finally the preferred xylooligosaccharides comprise a saccharide part consisting of 2 to 9 repeating units of structure {-[beta]-xyl-(1->4)-} (Suntory Co., Japan), for example.

The quantity of prebiotics in the frozen yoghurt composition according to the invention depends on their capacity to promote the development of lactic acid bacteria. As a general rule, the support may contain from 0.1 to 20% of such prebiotics (by weight relative to the dry matter content).

The frozen yoghurt composition may comprise an amount of non-replicating probiotics corresponding to an amount of at least $10^3$ cfu per g of prebiotic, preferably $10^4$ to $10^7$ cfu/g of prebiotic, for example.

The inventors were surprised to see that, e.g., in terms of an immune boosting effect and/or in terms of an anti-inflammatory effect non-replicating probiotic microorganisms may even be more effective than replicating probiotic microorganisms.

This is surprising since probiotics are often defined as "live micro-organisms that when administered in adequate amounts confer health benefits to the host" (FAO/WHO Guidelines). The vast majority of published literature deals with live probiotics. In addition, several studies investigated the health benefits delivered by non-replicating bacteria and most of them indicated that inactivation of probiotics, e.g. by heat treatment, leads to a loss of their purported health benefit (Rachmilewitz, D., et al., 2004, Gastroenterology 126:520-528; Castagliuolo, et al., 2005, FEMS Immunol. Med. Microbiol. 43:197-204; Gill, H. S, and K. J. Rutherfurd, 2001, Br. J. Nutr. 86:285-289; Kaila, M., et al., 1995, Arch. Dis. Child 72:51-53.). Some studies showed that killed probiotics may retain some health effects (Rachmilewitz, D., et al., 2004, Gastroenterology 126:520-528; Gill, H. S, and K. J. Rutherfurd, 2001, Br. J. Nutr. 86:285-289), but clearly, living probiotics were regarded in the art so far as more performing.

"Non-replicating" probiotic micro-organisms include probiotic bacteria which have been heat treated and probiotic bacteria which have been extruded. This includes micro-organisms that are inactivated, dead, non-viable and/or present as fragments such as DNA, metabolites, cytoplasmic compounds, and/or cell wall materials.

"Non-replicating" means that no viable cells and/or colony forming units can be detected by classical plating methods. Such classical plating methods are summarized in the microbiology book: James Monroe Jay, Martin J. Loessner, David A. Golden. 2005. Modern food microbiology. 7th edition, Springer Science, New York, N.Y. 790 p. Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h).

Probiotics are defined for the purpose of the present invention as "Microbial cell preparations or components of microbial cells with a beneficial effect on the health or well-being of the host." (Salminen S, Ouwehand A. Benno Y. et al "Probiotics: how should they be defined" Trends Food Sci. Technol. 1999:10 107-10).

The compositions of the present invention comprise probiotic micro-organisms and/or non-replicating probiotic micro-organisms in an amount sufficient to at least partially produce a health benefit. An amount adequate to accomplish this is defined as "a therapeutically effective dose". Amounts effective for this purpose will depend on a number of factors known to those of skill in the art such as the weight and general health state of the consumer, and on the effect of the food matrix.

In prophylactic applications, compositions according to the invention are administered to a consumer susceptible to or otherwise at risk of a disorder in an amount that is sufficient to at least partially reduce the risk of developing that disorder. Such an amount is defined to be "a prophylactic effective dose". Again, the precise amounts depend on a number of factors such as the consumer's state of health and weight, and on the effect of the food matrix.

Those skilled in the art will be able to adjust the therapeutically effective dose and/or the prophylactic effective dose appropriately.

In general the composition of the present invention contains non-replicating probiotic micro-organisms in a therapeutically effective dose and/or in a prophylactic effective dose.

Typically, the therapeutically effective dose and/or the prophylactic effective dose is in the range of about 0,005 mg-1000 mg non-replicating, probiotic micro-organisms per daily dose.

Preferably the non-replicating micro-organisms are present in an amount equivalent to between $10^4$ to $10^9$ cfu/g of dry composition, even more preferably in an amount equivalent to between $10^5$ and $10^9$ cfu/g of dry composition.

The probiotics may be rendered non-replicating by any method that is known in the art.

The technologies available today to render probiotic strains non-replicating are usually heat-treatment, γ-irradiation, UV light or the use of chemical agents (formalin, paraformaldehyde).

It has also been found that probiotic can be rendered bioactive non-replicating by applying a certain shear treatment such as that used in low temperature extrusion. Therefore, according to another embodiment, the probiotics are rendered non replicating by low temperature extrusion. Low temperature extrusion is commonly used in the art of frozen confectionery and designate extrusion at negative temperature, usually at temperatures below −11° C.

In terms of numerical amounts, e.g., "short-time high temperature" treated non-replicating micro-organisms may be present in the composition in an amount corresponding to between $10^4$ and $10^{12}$ equivalent cfu/g of the dry composition.

It would be preferred to use a technique to render probiotics non-replicating that is relatively easy to apply under industrial circumstances in the food industry.

Most products on the market today that contain probiotics are heat treated during their production. It would hence be convenient, to be able to heat treat probiotics either together with the produced product or at least in a similar way, while the probiotics retain or improve their beneficial properties or even gain a new beneficial property for the consumer.

However, inactivation of probiotic micro-organisms by heat treatments or by strong shear treatments such as those used in low temperature extrusion is associated in the literature generally with an at least partial loss of probiotic activity.

The present inventors have now surprisingly found, that rendering probiotic micro-organisms non-replicating, e.g., by heat treatment or by low temperature extrusion, does not result in the loss of probiotic health benefits, but—to the contrary—may enhance existing health benefits and even generate new health benefits.

Hence, one embodiment of the present invention is a frozen yoghurt composition wherein the non-replicating probiotic micro-organisms were rendered non-replicating by a heat-treatment and a second embodiment of the invention is a frozen yogurt composition wherein the non-replicating probiotic micro-organisms were rendered non-replicating by low temperature extrusion.

Regarding heat treatment, preferably, the heat treatment of the micro-organisms is carried out independently and the resulting non-replicating probiotic micro-organisms can then be added to the frozen yoghurt mix.

Such a heat treatment may be carried out at at least 71.5° C. for at least 1 second.

Long-term heat treatments or short-term heat treatments may be used.

In industrial scales today usually short term heat treatments, such as pasteurization are preferred. This kind of heat treatment reduces bacterial loads, and reduces the processing time, thereby reducing the spoiling of nutrients.

The inventors demonstrate for the first time that probiotics micro-organisms, heat treated at high temperatures for short times exhibit anti-inflammatory immune profiles regardless of their initial properties. In particular either a new anti-inflammatory profile is developed or an existing anti-inflammatory profile is enhanced by this heat treatment.

It is therefore now possible to generate non replicating probiotic micro-organisms with anti-inflammatory immune profiles by using specific heat treatment parameters that correspond to typical industrially applicable heat treatments, even if live counterparts are not anti-inflammatory strains.

Hence, for example, the heat treatment may be a high temperature treatment at about 71.5-150° C. for about 1-120 seconds. The high temperature treatment may be a high temperature/short time (HTST) treatment, high-heat Short-Time (HHST) or a ultra-high temperature (UHT) treatment.

The probiotic micro-organisms may be subjected to a high temperature treatment at about 71.5-150° C. for a short term of about 1-120 seconds.

More preferred the micro-organisms may be subjected to a high temperature treatment at about 90-140° C., for example 90°-120° C., for a short term of about 1-30 seconds.

This high temperature treatment renders the micro-organisms at least in part non-replicating.

The high temperature treatment may be carried out at normal atmospheric pressure but may be also carried out under high pressure. Typical pressure ranges are form 1 to 50 bar, preferably from 1-10 bar, even more preferred from 2 to 5 bar. Obviously, it is preferred if the probiotics are heat treated in a medium that is either liquid or solid, when the heat is applied. An ideal pressure to be applied will therefore depend on the nature of the composition which the micro-organisms are provided in and on the temperature used.

The high temperature treatment may be carried out in the temperature range of about 71.5-150° C., preferably of about 90-120° C., even more preferred of about 120-140° C.

The high temperature treatment may be carried out for a short term of about 1-120 seconds, preferably, of about 1-30 seconds, even more preferred for about 5-15 seconds.

This given time frame refers to the time the probiotic micro-organisms are subjected to the given temperature. Note, that depending on the nature and amount of the composition the micro-organisms are provided in and depending on the architecture of the heating apparatus used, the time of heat application may differ.

Typically, however, the composition of the present invention and/or the micro-organisms are treated by a high temperature short time (HTST) treatment, flash pasteurization or a ultra high temperature (UHT) treatment.

A UHT treatment is Ultra-high temperature processing or a ultra-heat treatment (both abbreviated UHT) involving the at least partial sterilization of a composition by heating it for a short time, around 1-10 seconds, at a temperature exceeding 135° C. (275° F.), which is the temperature required to kill bacterial spores in milk. For example, processing milk in this way using temperatures exceeding 135° C. permits a decrease of bacterial load in the necessary holding time (to 2-5 s) enabling a continuous flow operation.

There are two main types of UHT systems: the direct and indirect systems. In the direct system, products are treated by steam injection or steam infusion, whereas in the indirect system, products are heat treated using plate heat exchanger, tubular heat exchanger or scraped surface heat exchanger. Combinations of UHT systems may be applied at any step or at multiple steps in the process of product preparation.

A HTST treatment is defined as follows (High Temperature/Short Time): Pasteurization method designed to achieve a 5-log reduction, killing 99,9999% of the number of viable micro-organisms in milk. This is considered adequate for destroying almost all yeasts, molds and common spoilage bacteria and also to ensure adequate destruction of common pathogenic heat resistant organisms. In the HTST process milk is heated to 71.7° C. (161° F.) for 15-20 seconds.

Flash pasteurization is a method of heat pasteurization of perishable beverages like fruit and vegetable juices, beer and dairy products. It is done prior to filling into containers in order to kill spoilage micro-organisms, to make the products safer and extend their shelf life. The liquid moves in controlled continuous flow while subjected to temperatures of 71.5° C. (160° F.) to 74° C. (165° F.) for about 15 to 30 seconds.

For the purpose of the present invention the term "short time high temperature treatment" shall include high-temperature short time (HTST) treatments, UHT treatments, and flash pasteurization, for example.

Since such a heat treatment provides non-replicating probiotics with an improved anti-inflammatory profile, the composition of the present invention may be for use in the prevention or treatment of inflammatory disorders.

The inflammatory disorders that can be treated or prevented by the composition of the present invention are not particularly limited. For example, they may be selected from the group consisting of acute inflammations such as sepsis; burns; and chronic inflammation, such as inflammatory bowel disease, e.g., Crohn's disease, ulcerative colitis, pouchitis; necrotizing enterocolitis; skin inflammation, such as UV or chemical-induced skin inflammation, eczema, reactive skin; irritable bowel syndrome; eye inflammation; allergy, asthma; and combinations thereof.

If long term heat treatments are used to render the probiotic micro-organisms non-replicating, such a heat treatment may be carried out in the temperature range of about 70-150° C. for about 3 minutes-2 hours, preferably in the range of 80-140° C. from 5 minutes-40 minutes.

While the prior art generally teaches that bacteria rendered non-replicating by long-term heat-treatments are usually less efficient than live cells in terms of exerting their probiotic properties, the present inventors were able to demonstrate that heat-treated probiotics are superior in stimulating the immune system compared to their live counterparts.

The present invention relates also to a composition comprising probiotic micro-organisms that were rendered non-replicating by a heat treatment at at least about 70° C. for at least about 3 minutes.

The immune boosting effects of non-replicating probiotics were confirmed by in vitro immunoprofiling. The in vitro model used uses cytokine profiling from human Peripheral Blood Mononuclear Cells (PBMCs) and is well accepted in the art as standard model for tests of immunomodulating compounds (Schultz et al., 2003, Journal of Dairy Research 70, 165-173; Taylor et al., 2006, Clinical and Experimental Allergy, 36, 1227-1235; Kekkonen et al., 2008, World Journal of Gastroenterology, 14, 1192-1203)

The in vitro PBMC assay has been used by several authors/research teams for example to classify probiotics according to their immune profile, i.e. their anti- or pro-inflammatory characteristics (Kekkonen et al., 2008, World Journal of Gastroenterology, 14, 1192-1203). For example, this assay has been shown to allow prediction of an anti-inflammatory effect of probiotic candidates in mouse models of intestinal colitis (Foligne, B., et al., 2007, World J. Gastroenterol. 13:236-243). Moreover, this assay is regularly used as read-out in clinical trials and was shown to lead to results coherent with the clinical outcomes (Schultz et al., 2003, Journal of Dairy Research 70, 165-173; Taylor et al., 2006, Clinical and Experimental Allergy, 36, 1227-1235).

Allergic diseases have steadily increased over the past decades and they are currently considered as epidemics by WHO. In a general way, allergy is considered to result from an imbalance between the Th1 and Th2 responses of the immune system leading to a strong bias towards the production of Th2 mediators. Therefore, allergy can be mitigated, down-regulated or prevented by restoring an appropriate balance between the Th1 and Th2 arms of the immune system. This implies the necessity to reduce the Th2 responses or to enhance, at least transiently, the Th1 responses. The latter would be characteristic of an immune boost response, often accompanied by for example higher levels of IFNγ, TNF-α and IL-12. (Kekkonen et al., 2008, World Journal of Gastroenterology, 14, 1192-1203; Viljanen M. et al., 2005, Allergy, 60, 494-500)

The frozen yoghurt composition of the present invention allows it hence to treat or prevent disorders that are related to a compromised immune defence.

Consequently, the disorders linked to a compromised immune defence that can be treated or prevented by the composition of the present invention are not particularly limited.

For example, they may be selected from the group consisting of infections, in particular bacterial, viral, fungal and/or parasite infections; phagocyte deficiencies; low to severe immunodepression levels such as those induced by stress or immunodepressive drugs, chemotherapy or radiotherapy; natural states of less immunocompetent immune systems such as those of the neonates; allergies; and combinations thereof.

The frozen yoghurt composition described in the present invention allows it also to enhance a childs response to vaccines, in particular to oral vaccines.

According to a second embodiment, the non-replicating micro-organisms are rendered non-replicating by applying a strong shear treatment such as low temperature extrusion. Low temperature extrusion also referred to as low temperature freezing in the frozen confectionery area is for example described in U.S. Pat. No. 7,261,913, the content of which is here-included by reference. This treatment consists for example in applying a shear treatment with shear rates within the range of 1 to 50 l/s or the generation of shear stresses within the range of 2500 to 75000 Pa while maintaining a critical temperature in a screw extruder. The screw extruder may be such as that described in WO 2005/070225. The extrusion may be performed in a single or twin screw extruder.

In particular, non-replicating micro-organisms rendered non-replicating by low temperature extrusion show as well as the heat treatment anti-inflammatory benefit. Any amount of non-replicating micro-organisms will be effective. However, it is generally preferred, if at least 90%, preferably, at least 95%, more preferably at least 98%, most preferably at least 99%, ideally at least 99.9%, most ideally all of the probiotics are non-replicating.

In one embodiment of the present invention all micro-organisms are non-replicating.

Consequently, in the composition of the present invention at least 90%, preferably, at least 95%, more preferably at least 98%, most preferably at least 99%, ideally at least 99.9%, most ideally all of the probiotics may be non-replicating.

All probiotic micro-organisms may be used for the purpose of the present invention.

For example, the probiotic micro-organisms may be selected from the group consisting of bifidobacteria, lactobacilli, propionibacteria, or combinations thereof, for example *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli* and/or mixtures thereof.

The composition in accordance with the present invention may, for example comprise probiotic micro-organisms selected from the group consisting of *Bifidobacterium longum* NCC 3001, *Bifidobacterium longum* NCC 2705, *Bifidobacterium breve* NCC 2950, *Bifidobacterium lactis* NCC 2818, *Lactobacillus johnsonii* La1, *Lactobacillus paracasei* NCC 2461, *Lactobacillus rhamnosus* NCC 4007, *Lactobacillus reuteri* DSM17938, *Lactobacillus reuteri* ATCC55730, *Streptococcus themophilus* NCC 2019, *Streptococcus themophilus* NCC 2059, *Lactobacillus casei* NCC 4006, *Lactobacillus acidophilus* NCC 3009, *Lactobacillus casei* ACA-DC 6002 (NCC 1825), *Escherichia coli Nissle*, *Lactobacillus bulgaricus* NCC 15, *Lactococcus lactis* NCC 2287, or combinations thereof.

All these strains were either deposited under the Budapest treaty and/or are commercially available.

The strains have been deposited under the Budapest treaty as follows:

*Bifidobacterium longum* NCC 3001: ATCC BAA-999 (deposited on Jan. 29, 2001 at the Institut Pasteur, 28 rue du Docteur Roux, F-75024 Paris Cedex 15, France)

*Bifidobacterium longum* NCC 2705: CNCM I-2618

*Bifidobacterium breve* NCC 2950: CNCM I-3865 (deposited on Nov. 15, 2007 at the Institut Pasteur, 28 rue du Docteur Roux, F-75024 Paris Cedex 15, France)

*Bifidobacterium lactis* NCC 2818: CNCM I-3446 (deposited on Jun. 7, 2005 at the Institut Pasteur, 28 rue du Docteur Roux, F-75024 Paris Cedex 15, France)

*Lactobacillus paracasei* NCC 2461: CNCM I-2116 (deposited on Jan. 12, 1999 at the Institut Pasteur, 28 rue du Docteur Roux, F-75024 Paris Cedex 15, France)

*Lactobacillus rhamnosus* NCC 4007: CGMCC 1.3724 (deposited in October 2004 at the China General Microbiological Culture Collection Center, Chinese Academy of Sciences, P.O. Box 2714, Beijing, China 100080)

*Streptococcus themophilus* NCC 2019: CNCM I-1422 (deposited on May 18, 1994 at the Institut Pasteur, 28 rue du Docteur Roux, F-75024 Paris Cedex 15, France)

*Streptococcus themophilus* NCC 2059: CNCM I-4153 (deposited on Apr. 24, 2009 at the Institut Pasteur, 28 rue du Docteur Roux, F-75024 Paris Cedex 15, France)

*Lactococcus lactis* NCC 2287: CNCM I-4154 (deposited on Apr. 24, 2009 at the Institut Pasteur, 28 rue du Docteur Roux, F-75024 Paris Cedex 15, France)

*Lactobacillus casei* NCC 4006: CNCM I-1518 (deposited on Jun. 12, 2008 at the Institut Pasteur, 28 rue du Docteur Roux, F-75024 Paris Cedex 15, France)

*Lactobacillus casei* NCC 1825: ACA-DC 6002

*Lactobacillus acidophilus* NCC 3009: ATCC 700396

*Lactobacillus bulgaricus* NCC 15: CNCM I-1198 (deposited on Apr. 2, 1992 at the Institut Pasteur, 28 rue du Docteur Roux, F-75024 Paris Cedex 15, France)

*Lactobacillus johnsonii* La1: CNCM I-1225 (deposited on Jun. 30, 1992 at the Institut Pasteur, 28 rue du Docteur Roux, F-75024 Paris Cedex 15, France)

*Lactobacillus reuteri* DSM17938: DSM17938

*Lactobacillus reuteri* ATCC55730: ATCC55730

*Escherichia coli Nissle* 1917: DSM 6601

Strains named ATCC were deposited with the ATCC Patent Depository, 10801 University Blvd., Manassas, Va. 20110, USA.

Strains named CNCM were deposited with the COLLECTION NATIONALE DE CULTURES DE MICROORGANISMES (CNCM), 25 rue du Docteur Roux, F-75724 PARIS Cedex 15, France.

Strains named CGMCC were deposited with the China General Microbiological Culture Collection Center, Institute of Microbiology, Chinese Academy of Sciences, Zhongguancun, P.O. Box 2714, Beijing 100080, China.

Strains named ACA-DC were deposited with the Greek Coordinated Collections of Microorganisms, Dairy Laboratory, Department of Food Science and Technology, Agricultural University of Athens, 75, Iera odos, Botanikos, Athens, 118 55, Greece.

Strains named DSM were deposited with the DSMZ-Deutsche Sammlung von Mikroorganismen und Zellkulturen GmbH, Inhoffenstr. 7 Bˆ, 38124 Braunschweig, GERMANY.

Those skilled in the art will understand that they can freely combine all features of the present invention described herein, without departing from the scope of the invention as disclosed.

Further advantages and features of the present invention are apparent from the following Examples and Figures.

FIGS. 1A and B show the enhancement of the anti-inflammatory immune profiles of probiotics treated with "short-time high temperatures".

FIG. 2 shows non anti-inflammatory probiotic strains that become anti-inflammatory, i.e. that exhibit pronounced anti-inflammatory immune profiles in vitro after being treated with "short-time high temperatures".

FIGS. 3 A and B show probiotic strains in use in commercially available products that exhibit enhanced or new anti-inflammatory immune profiles in vitro after being treated with "short-time high temperatures".

FIGS. 4 A and B show dairy starter strains (i.e. Lc1 starter strains) that exhibits enhanced or new anti-inflammatory immune profiles in vitro upon heat treatment at high temperatures.

FIG. 5 shows a non anti-inflammatory probiotic strain that exhibits anti-inflammatory immune profiles in vitro after being treated with HTST treatments.

FIG. 6: Principal Component Analysis on PBMC data (IL-12p40, IFN-γ, TNF-α, IL-10) generated with probiotic and dairy starter strains in their live and heat treated (140° C. for 15 second) forms. Each dot represents one strain either live or heat treated identified by its NCC number or name.

NCC2950. Results are displayed as the percentage of diarrhea intensity (Mean±SEM calculated from 4 independent experiments) with 100% of diarrhea intensity corresponding to the symptoms developed in the positive control (sensitized and challenged by the allergen) group.

Figure 10:
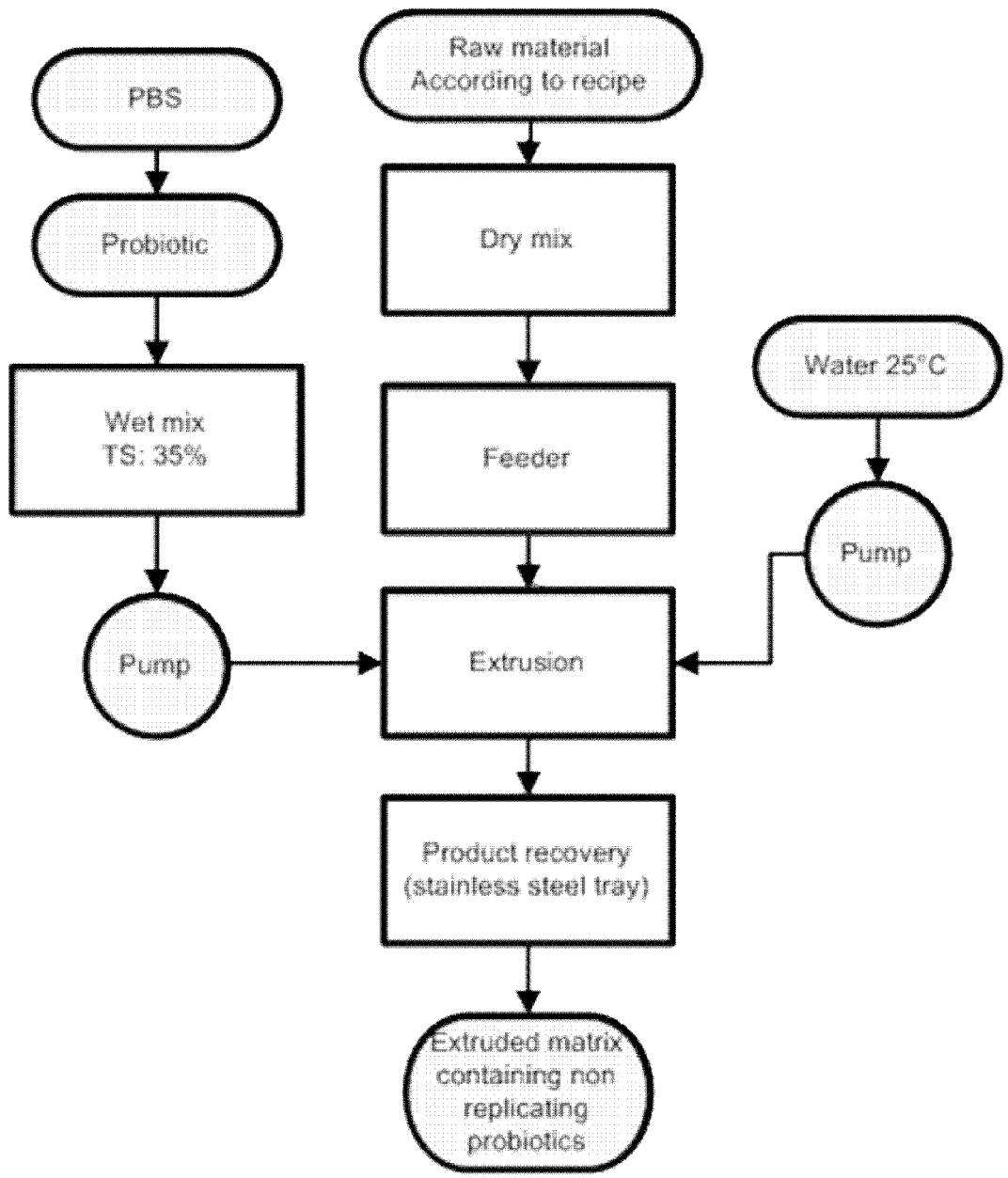

FIG. 10 shows a flowchart of the process used to generate an extruded matrix containing non replicating probiotic micro-organisms (probiotic micro-organisms injected as wet mix into the extruder).

Figure 11:
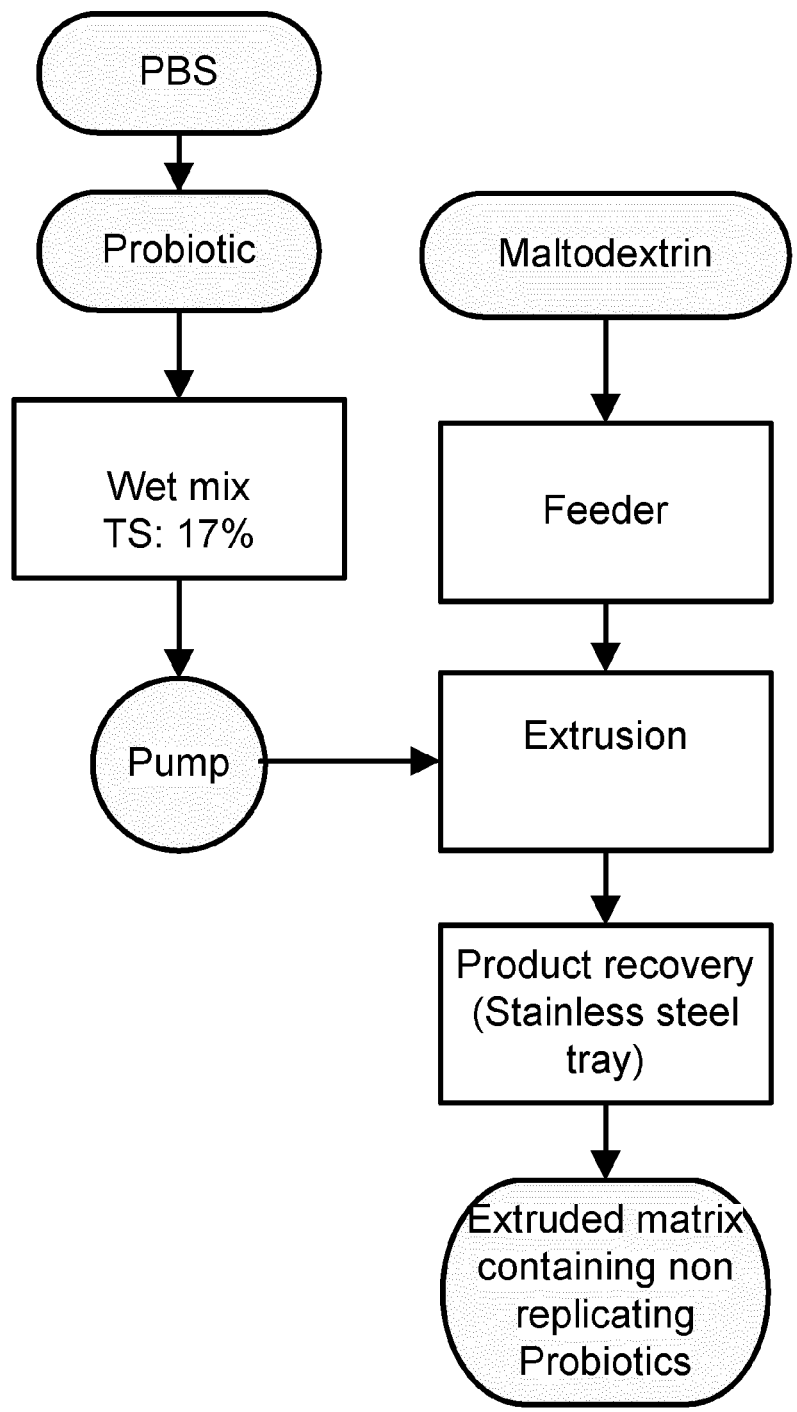

FIG. 11 shows a flowchart of the process used to generate an extruded matrix containing non replicating probiotic micro-organisms (probiotic micro-organisms injected as wet mix into the extruder) using cold extrusion.

Figure 12:
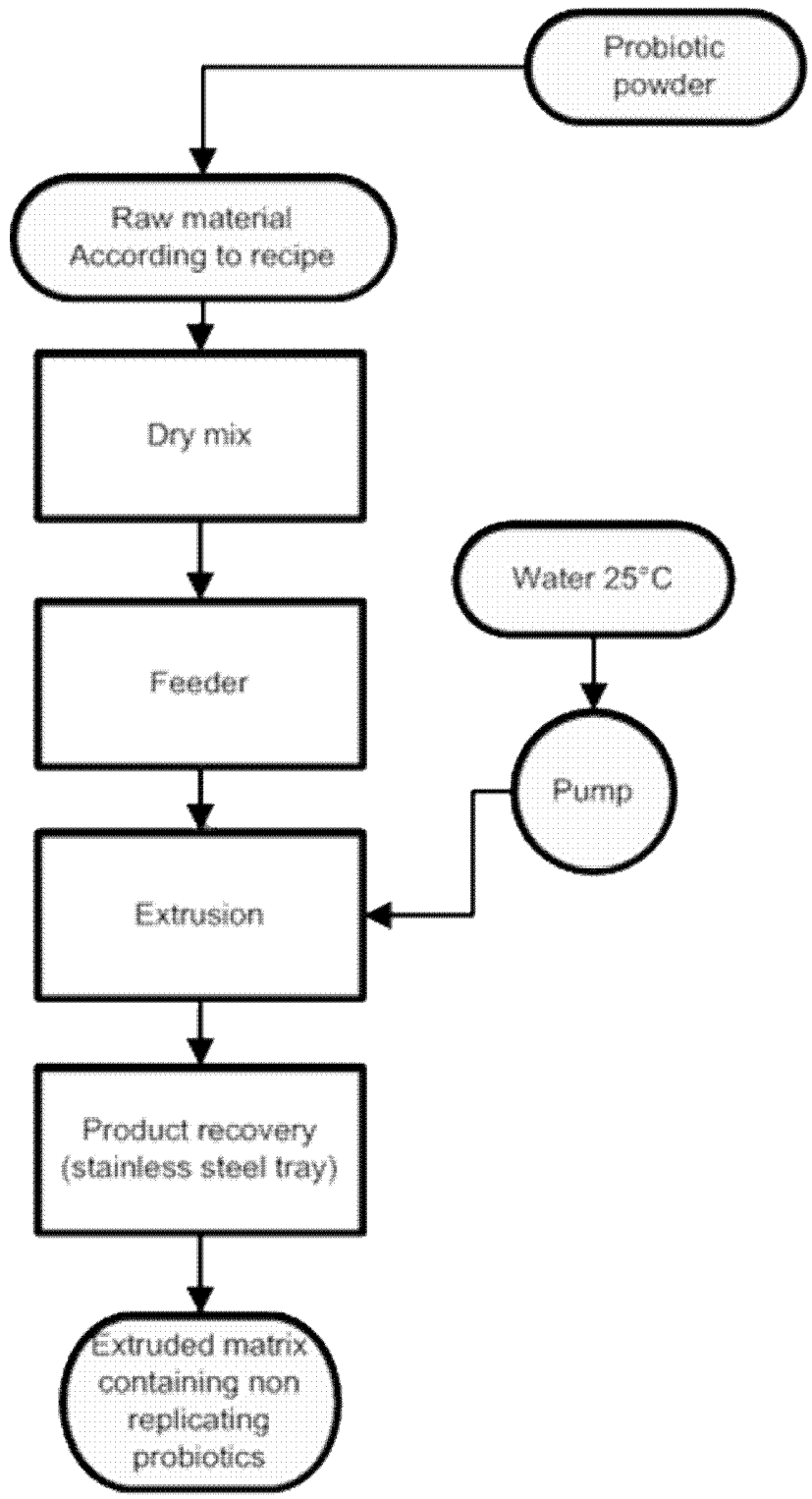

FIG. 12 shows a flowchart of an alternative process that can be used to generate an extruded matrix containing non replicating probiotic micro-organisms (probiotic micro-organisms are part of the dry mix).

Figure 13:
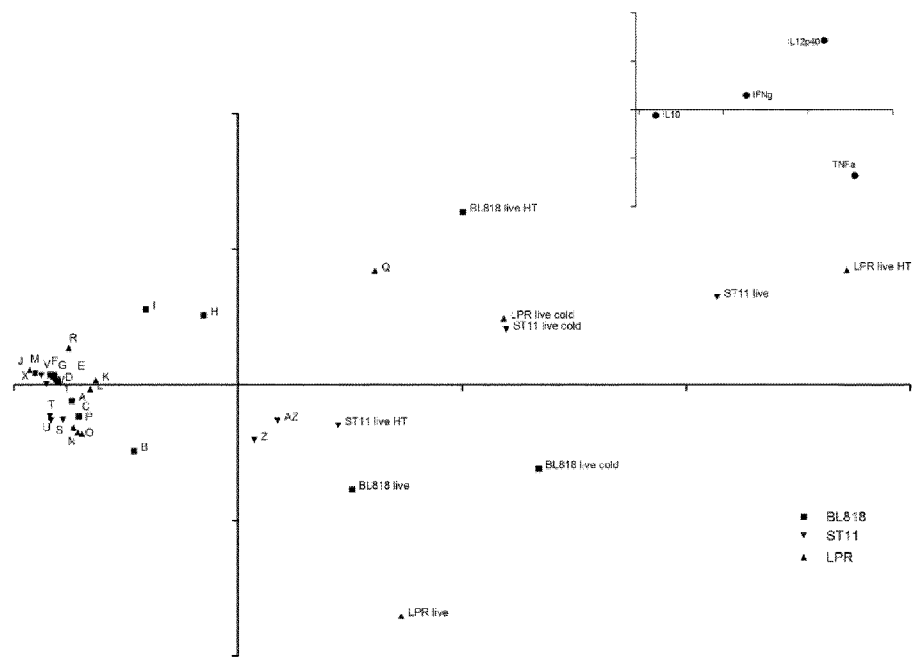

FIG. 13 shows the results of a PCA analysis of cytokine profiles of several extruded samples. Legend: A:BL818 800 rpm, B:BL818 1000 rpm, C:BL818 1200 rpm, D:BL818 85° C., E:BL818 100° C., F:BL818 120° C., G:BL818 140° C., H:BL818 120° C./15", I:BL818 140° C./15", J:LPR 800 rpm, K:LPR 1000 rpm, L:LPR 1200 rpm, M:LPR 85° C., N:LPR 100° C., O:LPR 120° C., P:LPR 140° C., Q:LPR 120° C./15", R:LPR 140° C./15", S:ST11 800 rpm, T:ST11 1000 rpm, U:ST11 1200 rpm, V:ST11 85° C., W:ST11 100° C., X:ST11 120° C., Y:ST11 140° C., Z:ST11 120° C./15", AZ:ST11 140° C./15".

Figure 14:
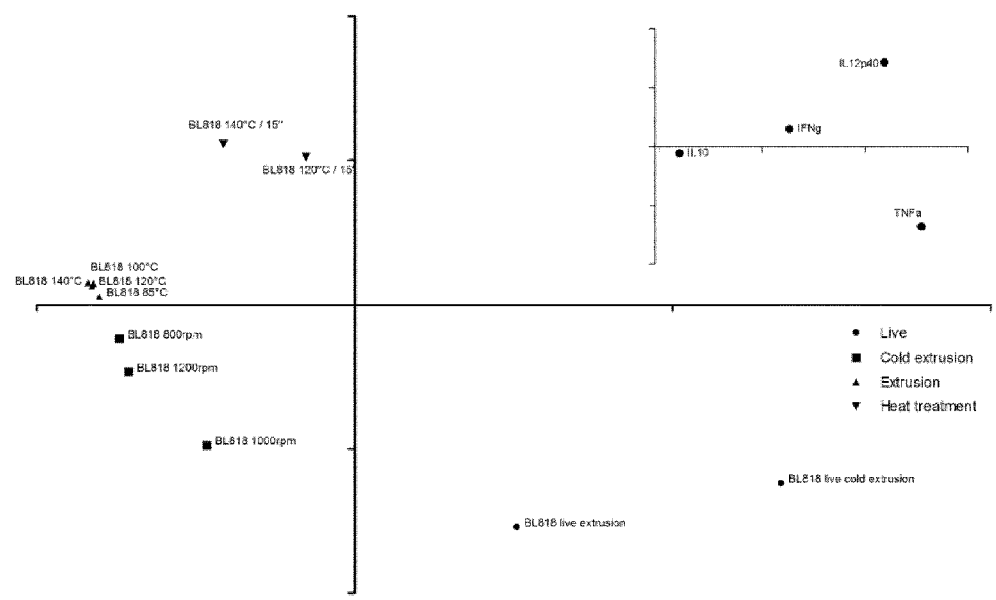

FIG. 14 shows the results of a PCA analysis on cytokine profiles for different extruded preparations of *B. longum* BL818.

Figure 15:
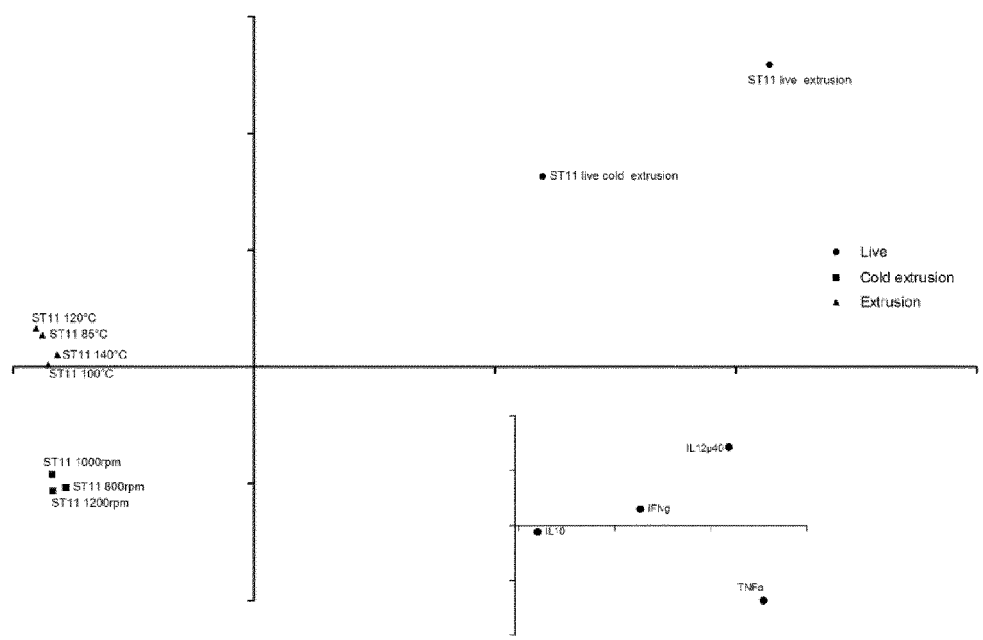

FIG. 15 shows the results of a PCA analysis on cytokine profiles for different extruded preparations of *L. paracasei* ST11.

EXAMPLE 1

Methodology

Bacterial Preparations:

The health benefits delivered by live probiotics on the host immune system are generally considered to be strain specific. Probiotics inducing high levels of IL-10 and/or inducing low levels of pro-inflammatory cytokines in vitro (PBMC assay) have been shown to be potent anti-inflammatory strains in vivo (Foligné, B., et al., 2007, World J. Gastroenterol. 13:236-243).

Several probiotic strains were used to investigate the anti-inflammatory properties of heat treated probiotics. These were *Bifidobacterium longum* NCC 3001, *Bifidobacterium longum* NCC 2705, *Bifidobacterium breve* NCC 2950, *Bifidobacterium lactis* NCC 2818, *Lactobacillus paracasei* NCC 2461, *Lactobacillus rhamnosus* NCC 4007, *Lactobacillus casei* NCC 4006, *Lactobacillus acidophilus* NCC 3009, *Lactobacillus casei* ACA-DC 6002 (NCC 1825), and *Escherichia coli* Nissle. Several starter culture strains including some strains commercially used to produce Nestlé Lc1 fermented products were also tested: *Streptococcus thermophilus* NCC 2019, *Streptococcus thermophilus* NCC 2059, *Lactobacillus bulgaricus* NCC 15 and *Lactococcus lactis* NCC 2287.

Bacterial cells were cultivated in conditions optimized for each strain in 5-15 L bioreactors. All typical bacterial growth media are usable. Such media are known to those skilled in the art. When pH was adjusted to 5.5, 30% base solution (either NaOH or $Ca(OH)_2$) was added continuously. When adequate, anaerobic conditions were maintained by gassing headspace with $CO_2$. *E. coli* was cultivated under standard aerobic conditions.

Bacterial cells were collected by centrifugation (5,000×g, 4° C.) and re-suspended in phosphate buffer saline (PBS) in adequate volumes in order to reach a final concentration of around $10^9$-$10^{10}$ cfu/ml. Part of the preparation was frozen at −80° C. with 15% glycerol. Another part of the cells was heat treated by:

Ultra High Temperature: 140° C. for 15 sec; by indirect steam injection.

High Temperature Short Time (HTST): 74° C., 90° C. and 120° C. for 15 sec by indirect steam injection Long Time Low Temperature (85° C., 20 min) in water bath Upon heat treatment, samples were kept frozen at −80° C. until use.

In Vitro Immunoprofiling of Bacterial Preparations:

The immune profiles of live and heat treated bacterial preparations (i.e. the capacity to induce secretion of specific cytokines from human blood cells in vitro) were assessed. Human peripheral blood mononuclear cells (PBMCs) were isolated from blood filters. After separation by cell density gradient, mononuclear cells were collected and washed twice with Hank's balanced salt solution. Cells were then resuspended in Iscove's Modified Dulbecco's Medium (IMDM, Sigma) supplemented with 10% foetal calf serum (Bioconcept, Paris, france), 1% L-glutamine (Sigma), 1% penicillin/streptomycin (Sigma) and 0.1% gentamycin (Sigma). PBMCs ($7×10^5$ cells/well) were then incubated with live and heat treated bacteria (equivalent $7×10^6$ cfu/well) in 48 well plates for 36 h. The effects of live and heat treated bacteria were tested on PBMCs from 8 individual donors splitted into two separated experiments. After 36 h incubation, culture plates were frozen and kept at −20° C. until cytokine measurement. Cytokine profiling was performed in parallel (i.e. in the same experiment on the same batch of PBMCs) for live bacteria and their heat-treated counterparts.

Levels of cytokines (IFN-γ, IL-12p40, TNF-α and IL-10) in cell culture supernatants after 36 h incubation were determined by ELISA (R&D DuoSet Human IL-10, BD OptEIA Human IL12p40, BD OptEIA Human TNFα, BD OptEIA Human I FN-γ) following manufacturer's instructions. IFN-γ, IL-12p40 and TNF-α are pro-inflammatory cytokines, whereas IL-10 is a potent anti-inflammatory mediator. Results are expressed as means (pg/ml)+/−SEM of 4 individual donors and are representative of two individual experiments performed with 4 donors each. The ratio IL-12p40/IL-10 is calculated for each strain as a predictive value of in vivo anti-inflammatory effect (Foligné, B., et al., 2007, World J. Gastroenterol. 13:236-243).

Numerical cytokine values (pg/ml) determined by ELISA (see above) for each strain were transferred into BioNumerics v5.10 software (Applied Maths, Sint-Martens-Latem, Belgium). A Principal Component Analysis (PCA, dimensioning technique) was performed on this set of data. Subtraction of the averages over the characters and division by the variances over the characters were included in this analysis.

Results

Figure 4A:
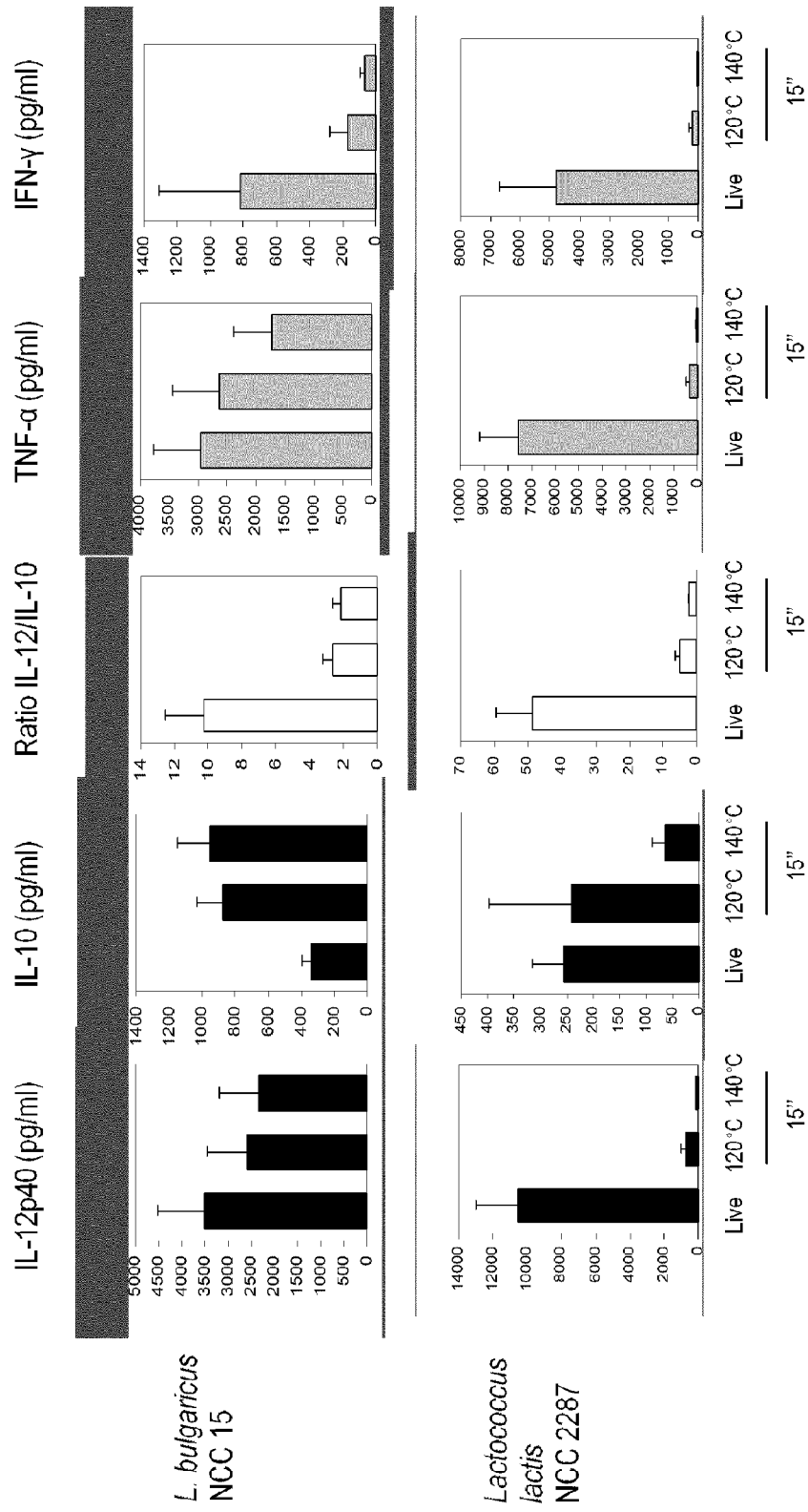
Figure 4B:
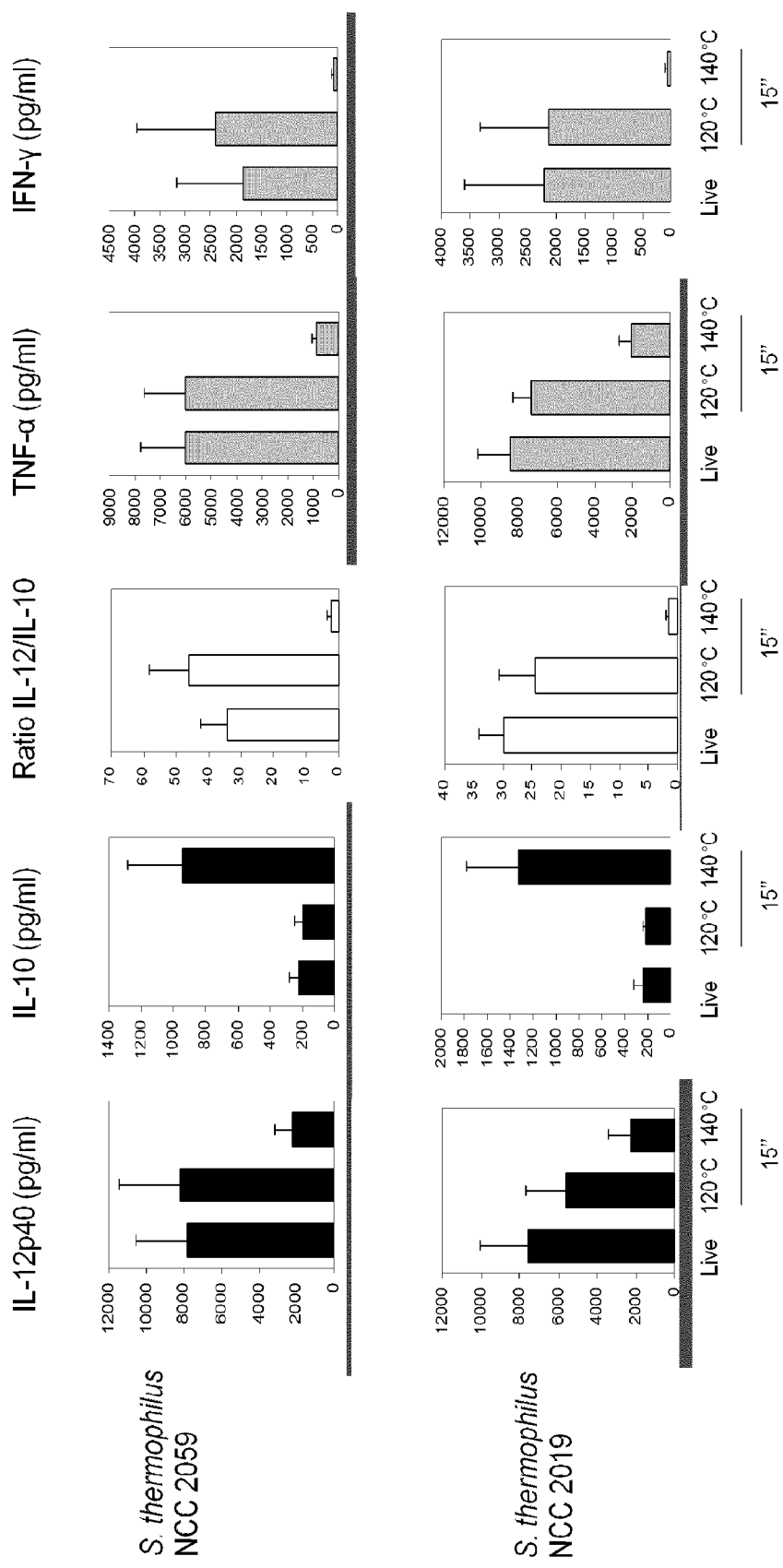
Figure 5:
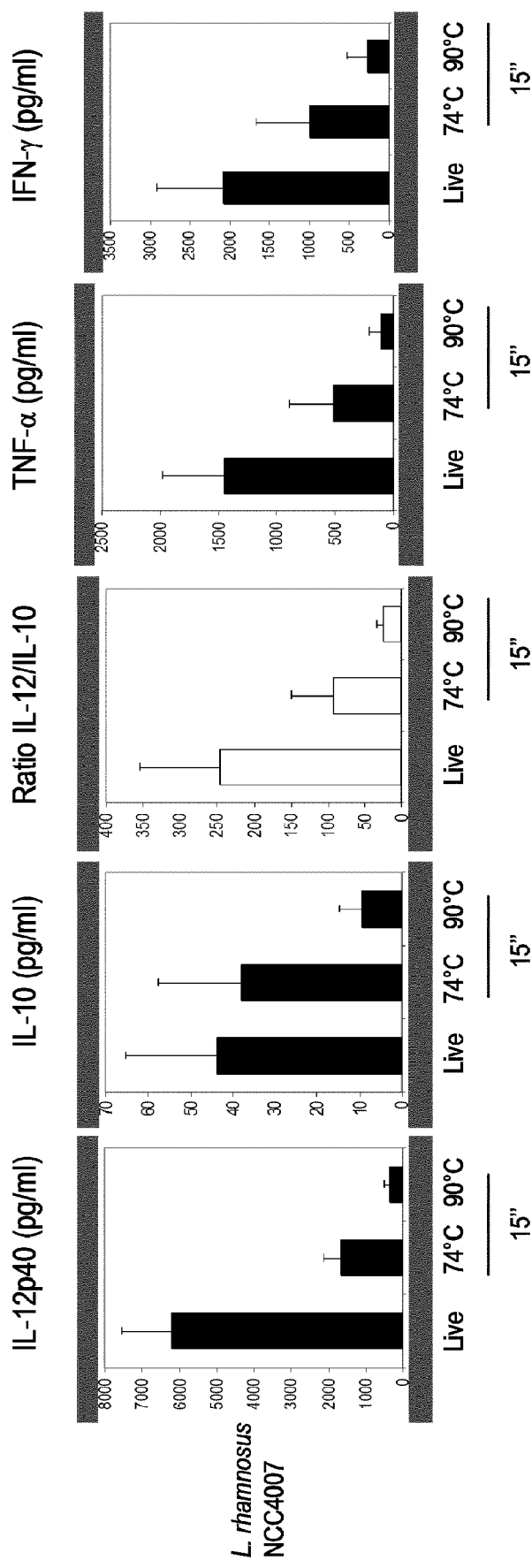
Figure 6:
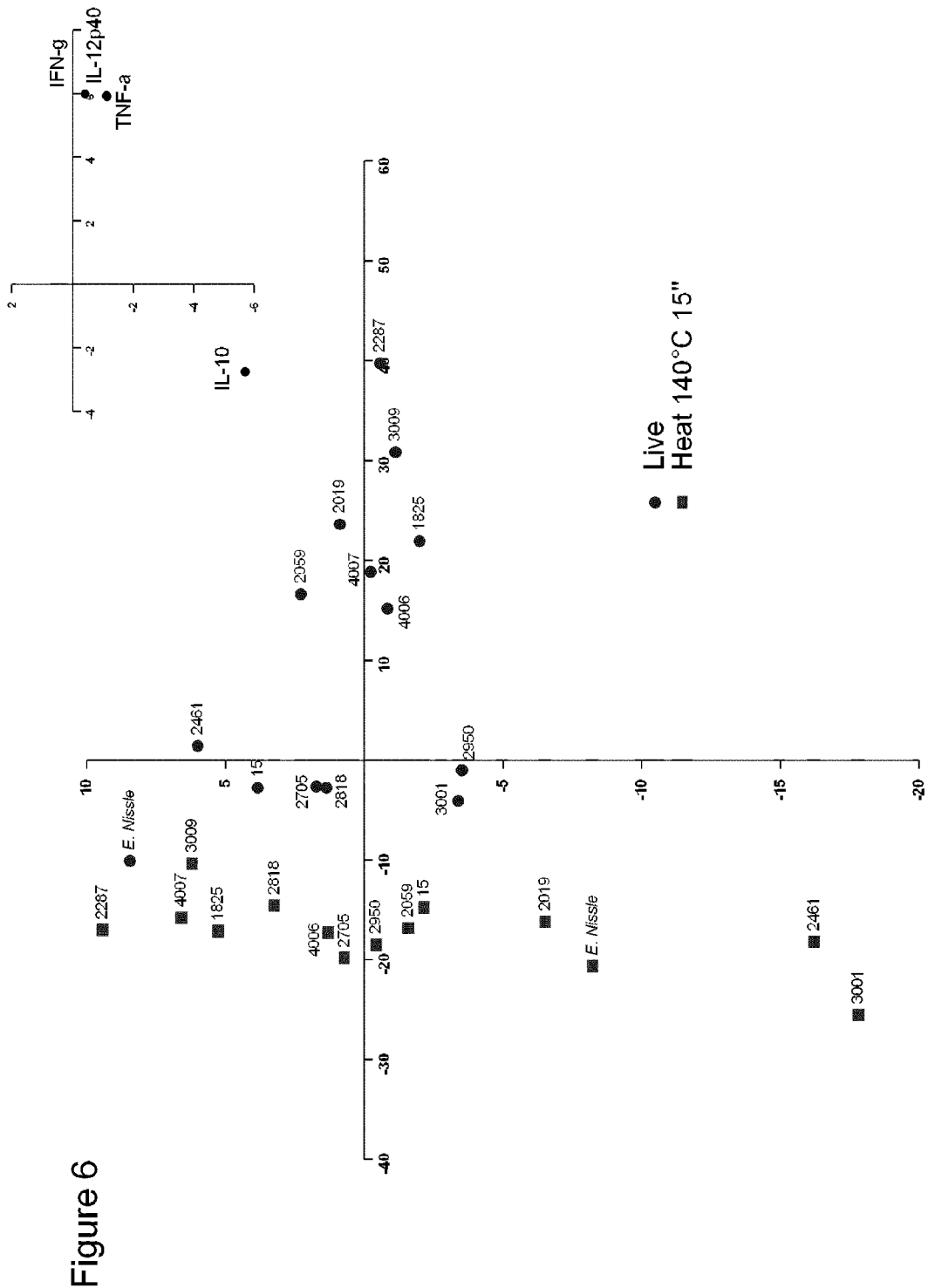
Figure 7:
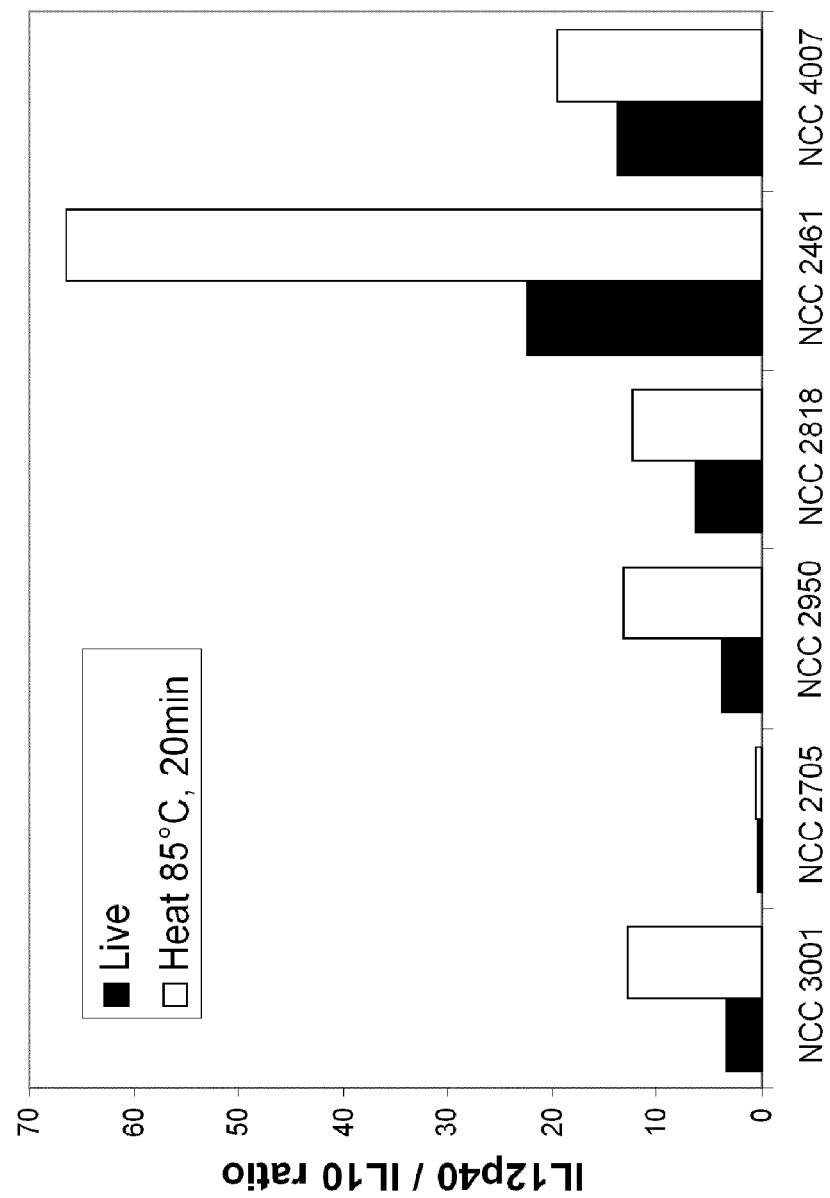
FIG. 7 shows IL-12p40/IL-10 ratios of live and heat treated (85° C., 20 min) strains. Overall, heat treatment at 85° C. for 20 min leads to an increase of IL-12p40/IL-10 ratios as opposed to "short-time high temperature" treatments of the present invention (FIGS. 1, 2, 3, 4 and 5).

Anti-inflammatory profiles generated by Ultra High Temperature (UHT)/High Temperature Short Time (HTST)-like treatments The probiotic strains under investigation were submitted to a series of heat treatments (Ultra High Temperature (UHT), High Temperature Short Time (HTST) and 85° C. for 20 min) and their immune profiles were compared to those of live cells in vitro. Live micro-organisms (probiotics and/or dairy starter cultures) induced different levels of cytokine production when incubated with human PBMC (FIGS. 1, 2, 3, 4 and 5). Heat treatment of these micro-organisms modified the levels of cytokines produced by PBMC in a temperature dependent manner. "Short-time high temperature" treatments (120° C. or 140° C. for 15") generated non replicating bacteria with anti-inflammatory immune profiles (FIGS. 1, 2, 3 and 4). Indeed, UHT-like treated strains (140° C., 15 sec) induced less pro-inflammatory cytokines (TNF-α, IFN-γ, IL-12p40) while maintaining or inducing additional IL-10 production (compared to live counterparts). The resulting IL-12p40/IL-10 ratios were lower for any UHT-like treated strains compared to live cells (FIGS. 1, 2, 3 and 4). This observation was also valid for bacteria treated by HTST-like treatments, i.e. submitted to 120° C. for 15 sec (FIGS. 1, 2, 3 and 4), or 74° C. and 90° C. for 15 sec (FIG. 5). Heat treatments (UHT-like or HTST-like treatments) had a similar effect on in vitro immune profiles of probiotic strains (FIGS. 1, 2, 3 and 5) and dairy starter cultures (FIG. 4). Principal Component Analysis on PBMC data generated with live and heat treated (140° C., 15") probiotic and dairy starter strains revealed that live strains are spread all along the x axis, illustrating that strains exhibit very different immune profiles in vitro, from low (left side) to high (right side) inducers of pro-inflammatory cytokines. Heat treated strains cluster on the left side of the graph, showing that pro-inflammatory cytokines are much less induced by heat treated strains (FIG. 6). By contrast, bacteria heat treated at 85° C. for 20 min induced more pro-inflammatory cytokines and less IL-10 than live cells resulting in higher IL-12p40/IL-10 ratios (FIG. 7).

Anti-inflammatory profiles are enhanced or generated by UHT-like and HTST-like treatments.

Figure 1A:
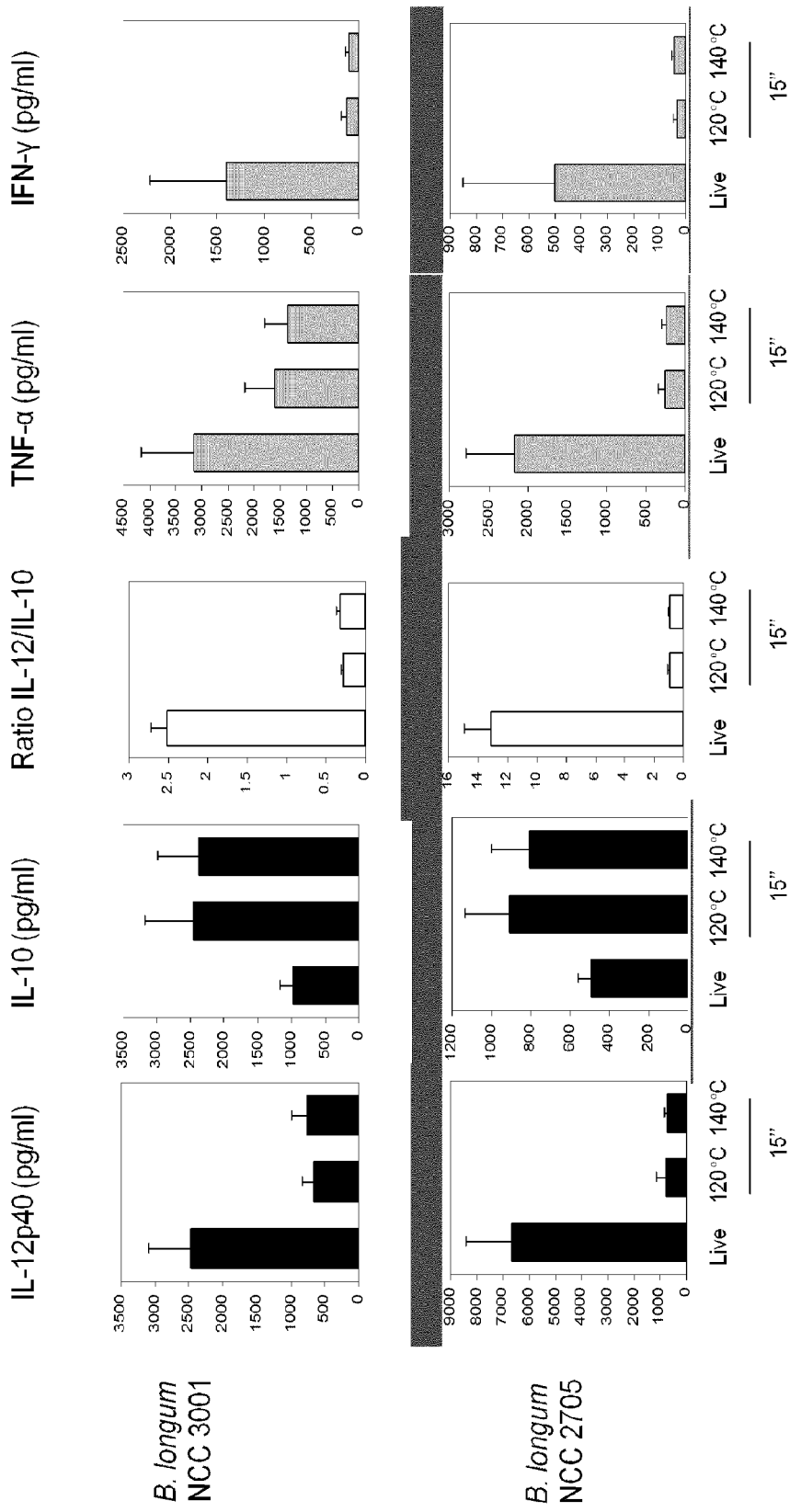
Figure 1B:
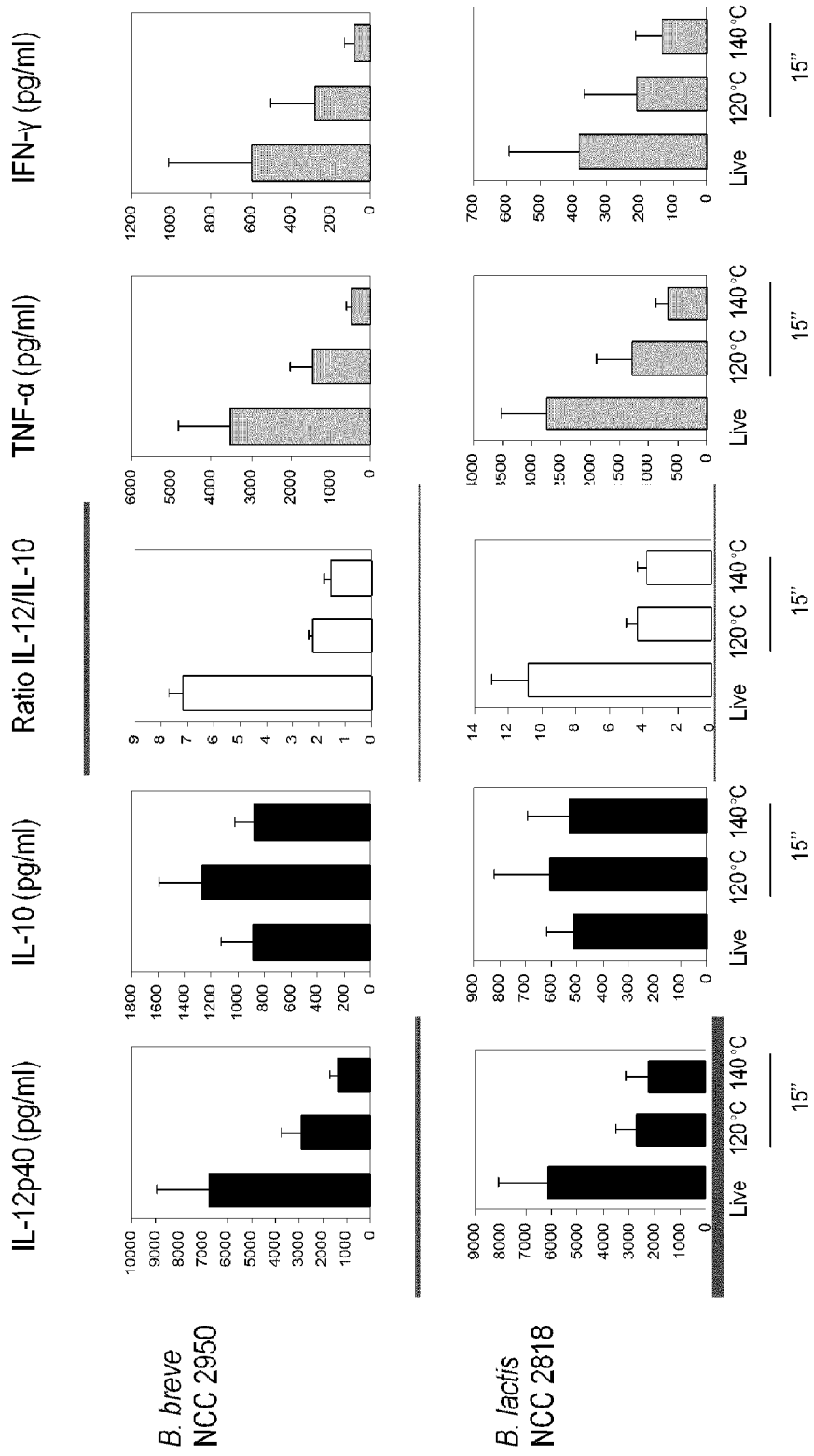
Figure 2:
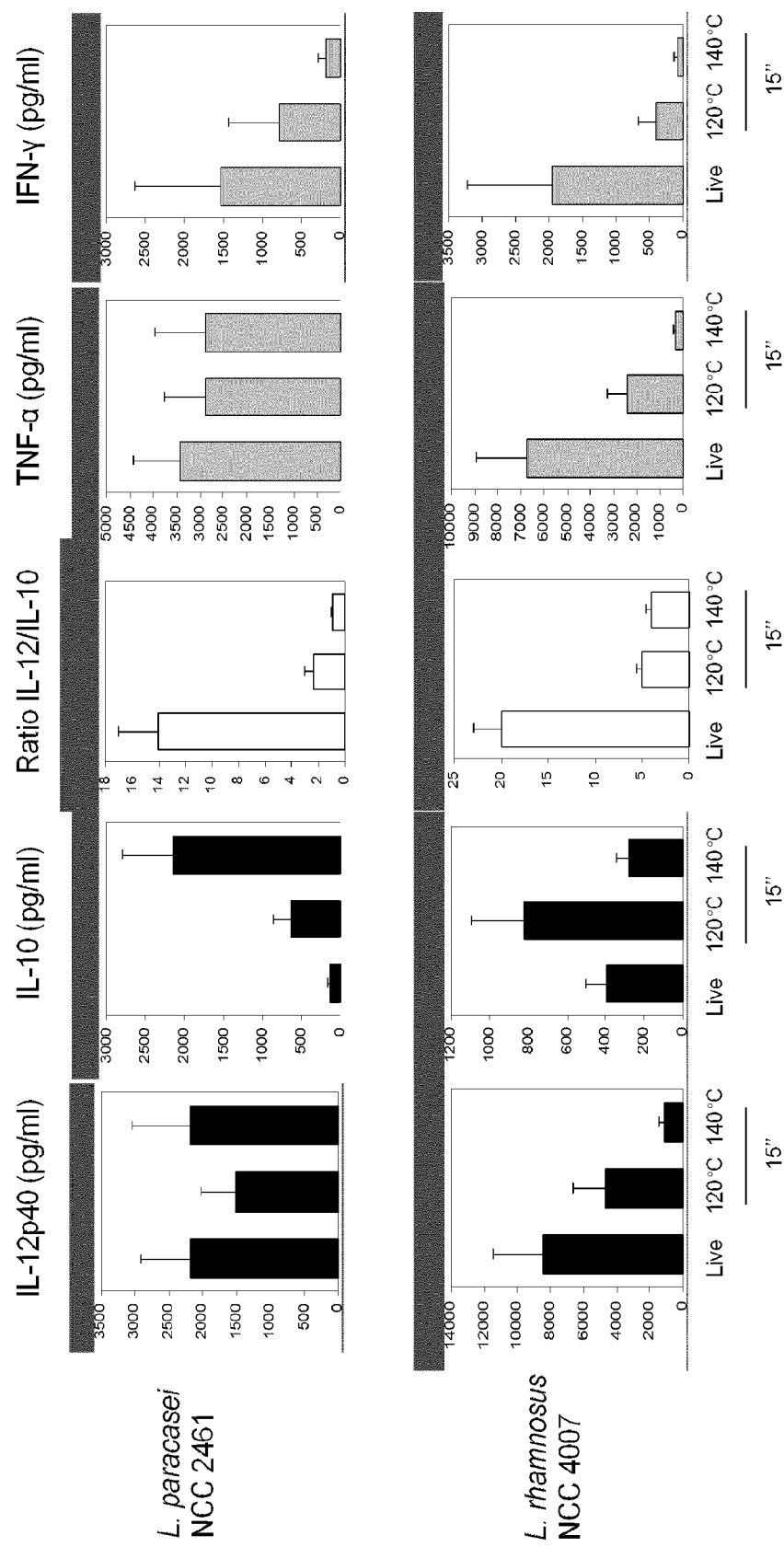
Figure 3A:
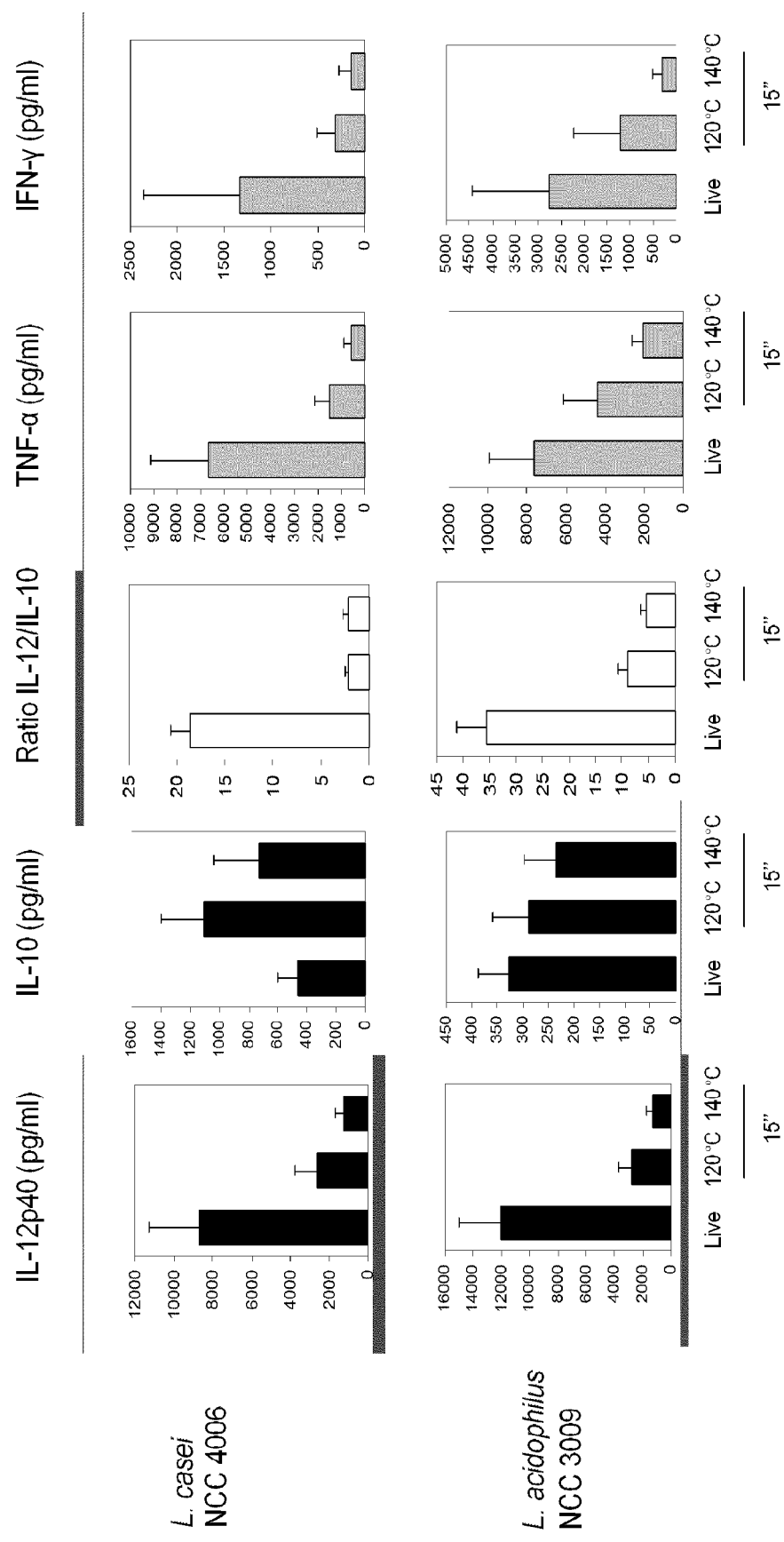
Figure 3B:
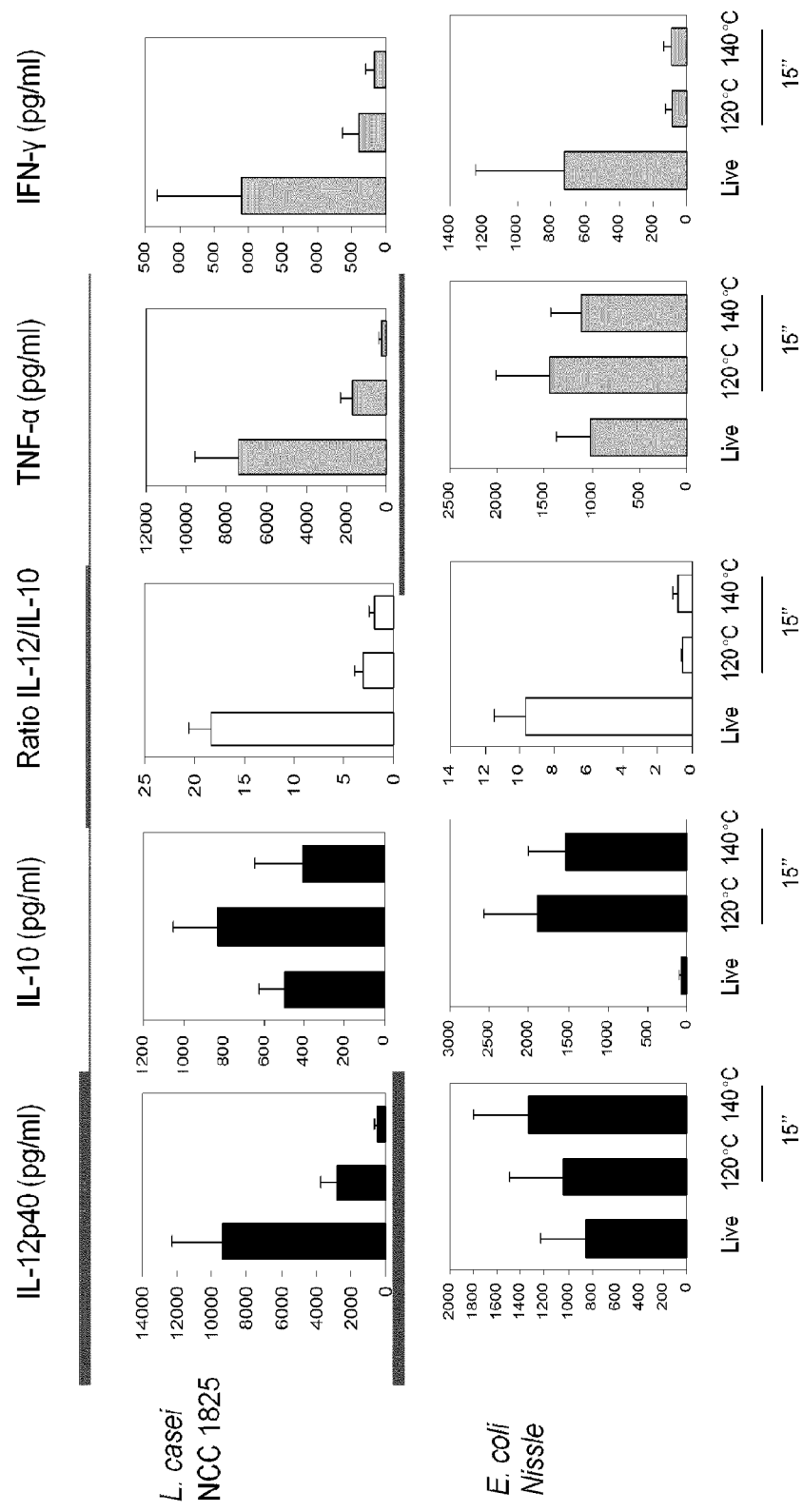

UHT and HTST treated strains exhibit anti-inflammatory profiles regardless of their respective initial immune profiles (live cells). Probiotic strains known to be anti-inflammatory in vivo and exhibiting anti-inflammatory profiles in vitro (*B. longum* NCC 3001, *B. longum* NCC 2705, *B. breve* NCC 2950, *B. lactis* NCC 2818) were shown to exhibit enhanced anti-inflammatory profiles in vitro after "short-time high temperature" treatments. As shown in FIG. 1, the IL-12p40/IL-10 ratios of UHT-like treated *Bifidobacterium* strains were lower than those from the live counterparts, thus showing improved anti-inflammatory profiles of UHT-like treated samples. More strikingly, the generation of anti-inflammatory profiles by UHT-like and HTST-like treatments was also confirmed for non anti-inflammatory live strains. Both live *L. rhamnosus* NCC 4007 and *L. paracasei* NCC 2461 exhibit high IL-12p40/IL-10 ratios in vitro (FIGS. 2 and 5). The two live strains were shown to be not protective against TNBS-induced colitis in mice. The IL-12p40/IL-10 ratios induced by *L. rhamnosus* NCC 4007 and *L. paracasei* NCC 2461 were dramatically reduced after "short-time high temperature" treatments (UHT or HTST) reaching levels as low as those obtained with *Bifidobacterium* strains. These low IL-12p40/IL-10 ratios are due to low levels of IL-12p40 production combined with no change (*L. rhamnosus* NCC 4007) or a dramatic induction of IL-10 secretion (*L. paracasei* NCC 2461) (FIG. 2).

As a Consequence:
Anti-inflammatory profiles of live micro-organisms can be enhanced by UHT-like and HTST-like heat treatments (for instance *B. longum* NCC 2705, *B. longum* NCC 3001, *B. breve* NCC 2950, *B. lactis* NCC 2818)
Anti-inflammatory profiles can be generated from non anti-inflammatory live micro-organisms (for example *L. rhamnosus* NCC 4007, *L. paracasei* NCC 2461, dairy starters *S. thermophilus* NCC 2019) by UHT-like and HTST-like heat treatments.

Anti-inflammatory profiles were also demonstrated for strains isolated from commercially available products (FIGS. 3 A & B) including a probiotic *E. coli* strain.

The impact of UHT/HTST-like treatments was similar for all tested probiotics and dairy starters, for example lactobacilli, bifidobacteria and streptococci.

UHT/HTST-like treatments were applied to several lactobacilli, bifidobacteria and streptococci exhibiting different in vitro immune profiles. All the strains induced less pro-inflammatory cytokines after UHT/HTST-like treatments than their live counterparts (FIGS. 1, 2, 3, 4, 5 and 6) demonstrating that the effect of UHT/HTST-like treatments on the immune properties of the resulting non replicating bacteria can be generalized to all probiotics, in particular to lactobacilli and bifidobacteria and specific *E. coli* strains and to all dairy starter cultures in particular to streptococci, lactococci and lactobacilli.

EXAMPLE 2

Methodology

Bacterial Preparations:
Five probiotic strains were used to investigate the immune boosting properties of non-replicating probiotics: 3 bifidobacteria (*B. longum* NCC3001, *B. lactis* NCC2818, *B. breve* NCC2950) and 2 lactobacilli (*L. paracasei* NCC2461, *L. rhamnosus* NCC4007).

Bacterial cells were grown on MRS in batch fermentation at 37° C. for 16-18 h without pH control. Bacterial cells were spun down (5,000×g, 4° C.) and resuspended in phosphate buffer saline prior to be diluted in saline water in order to reach a final concentration of around 10E10 cfu/ml. *B. longum* NCC3001, *B. lactis* NCC2818, *L. paracasei* NCC2461, *L. rhamnosus* NCC4007 were heat treated at 85° C. for 20 min in a water bath. *B. breve* NCC2950 was heat treated at 90° C. for 30 minutes in a water bath. Heat treated bacterial suspensions were aliquoted and kept frozen at −80° C. until use. Live bacteria were stored at −80° C. in PBS-glycerol 15% until use.

In Vitro Immunoprofiling of Bacterial Preparations
The immune profiles of live and heat treated bacterial preparations (i.e. the capacity to induce secretion of specific cytokines from human blood cells in vitro) were assessed. Human peripheral blood mononuclear cells (PBMCs) were isolated from blood filters. After separation by cell density gradient, mononuclear cells were collected and washed twice with Hank's balanced salt solution. Cells were then resuspended in Iscove's Modified Dulbecco's Medium (IMDM, Sigma) supplemented with 10% foetal calf serum (Bioconcept, Paris, france), 1% L-glutamine (Sigma), 1% penicillin/streptomycin (Sigma) and 0.1% gentamycin (Sigma). PBMCs ($7 \times 10^5$ cells/well) were then incubated with live and heat treated bacteria (equivalent $7 \times 10^6$ cfu/well) in 48 well plates for 36 h. The effects of live and heat treated bacteria were tested on PBMCs from 8 individual donors splitted into two separate experiments. After 36 h incubation, culture plates were frozen and kept at −20° C. until cytokine measurement.

Cytokine profiling was performed in parallel (i.e. in the same experiment on the same batch of PBMCs) for live bacteria and their heat-treated counterparts.

Levels of cytokines (IFN-γ, IL-12p40, TNF-α and IL-10) in cell culture supernatants after 36 h incubation were determined by ELISA (R&D DuoSet Human IL-10, BD OptEIA Human IL12p40, BD OptEIA Human TNF, BD OptEIA Human IFN-γ) following manufacturer's instructions. IFN-γ, IL-12p40 and TNF-α are pro-inflammatory cytokines, whereas IL-10 is a potent anti-inflammatory mediator. Results are expressed as means (pg/ml)+/− SEM of 4 individual donors and are representative of two individual experiments performed with 4 donors each.

In Vivo Effect of Live and Heat Treated *Bifidobacterium breve* NCC2950 in Prevention of Allergic Diarrhea A mouse model of allergic diarrhea was used to test the Th1 promoting effect of *B. breve* NCC2950 (Brandt E. B et al. JCI 2003; 112(11): 1666-1667). Following sensitization (2 intraperitoneal injections of Ovalbumin (OVA) and aluminium potassium sulphate at an interval of 14 days; days 0 and 14) male Balb/c mice were orally challenged with OVA for 6 times (days 27, 29, 32, 34, 36, 39) resulting in transient clinical symptoms (diarrhea) and changes of immune parameters (plasma concentration of total IgE, OVA specific IgE, mouse mast cell protease 1, i.e MMCP-1). *Bifidobacterium breve* NCC2950 live or heat treated at 90° C. for 30 min, was administered by gavage 4 days prior to OVA sensitization (days −3, −2, −1, 0 and days 11, 12, 13 and 14) and during the challenge period (days 23 to 39). A daily bacterial dose of around $10^9$ colony forming units (cfu) or equivalent cfu/mouse was used.

Results

Induction of Secretion of 'Pro-Inflammatory' Cytokines after Heat Treatment

The ability of heat treated bacterial strains to stimulate cytokine secretion by human peripheral blood mononuclear cells (PBMCs) was assessed in vitro. The immune profiles based on four cytokines upon stimulation of PBMCs by heat treated bacteria were compared to that induced by live bacterial cells in the same in vitro assay.

The heat treated preparations were plated and assessed for the absence of any viable counts. Heat treated bacterial preparations did not produce colonies after plating.

Figure 8:
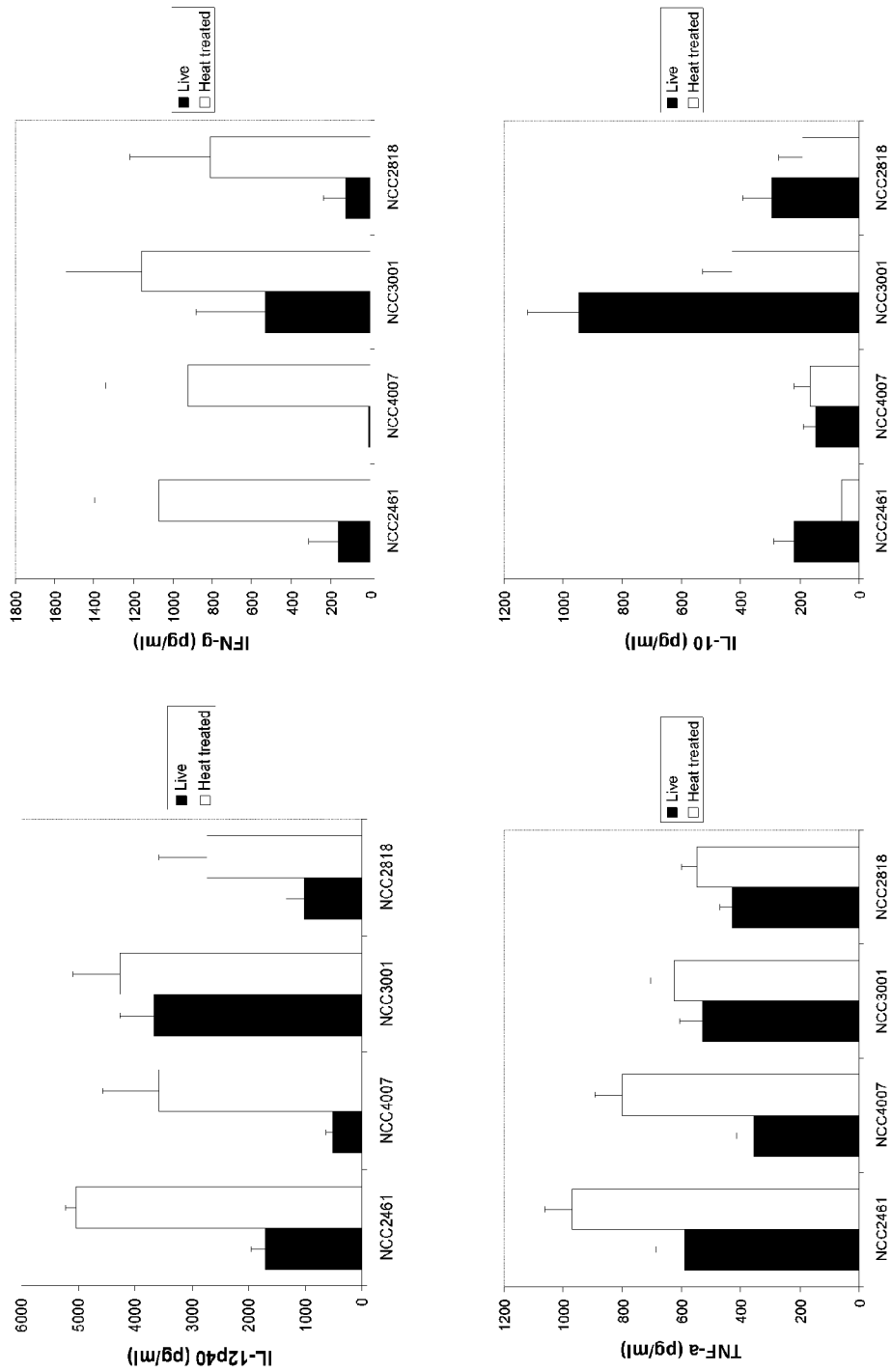
FIG. 8 shows the enhancement of in vitro cytokine secretion from human PBMCs stimulated with heat treated bacteria.

Live probiotics induced different and strain dependent levels of cytokine production when incubated with human PBMCs (FIG. 8). Heat treatment of probiotics modified the levels of cytokines produced by PBMCs as compared to their live counterparts. Heat treated bacteria induced more pro-inflammatory cytokines (TNF-α, IFN-γ, IL-12p40) than their live counterparts do. By contrast heat treated bacteria induced similar or lower amounts of IL-10 compared to live cells (FIG. 8). These data show that heat treated bacteria are more able to stimulate the immune system than their live counterparts and therefore are more able to boost weakened immune defences. In other words the in vitro data illustrate an enhanced immune boost effect of bacterial strains after heat treatment.

In order to illustrate the enhanced effect of heat-treated *B. breve* NCC2950 (compared to live cells) on the immune system, both live and heat treated *B. breve* NCC2950 (strain A) were tested in an animal model of allergic diarrhea.

Figure 9:
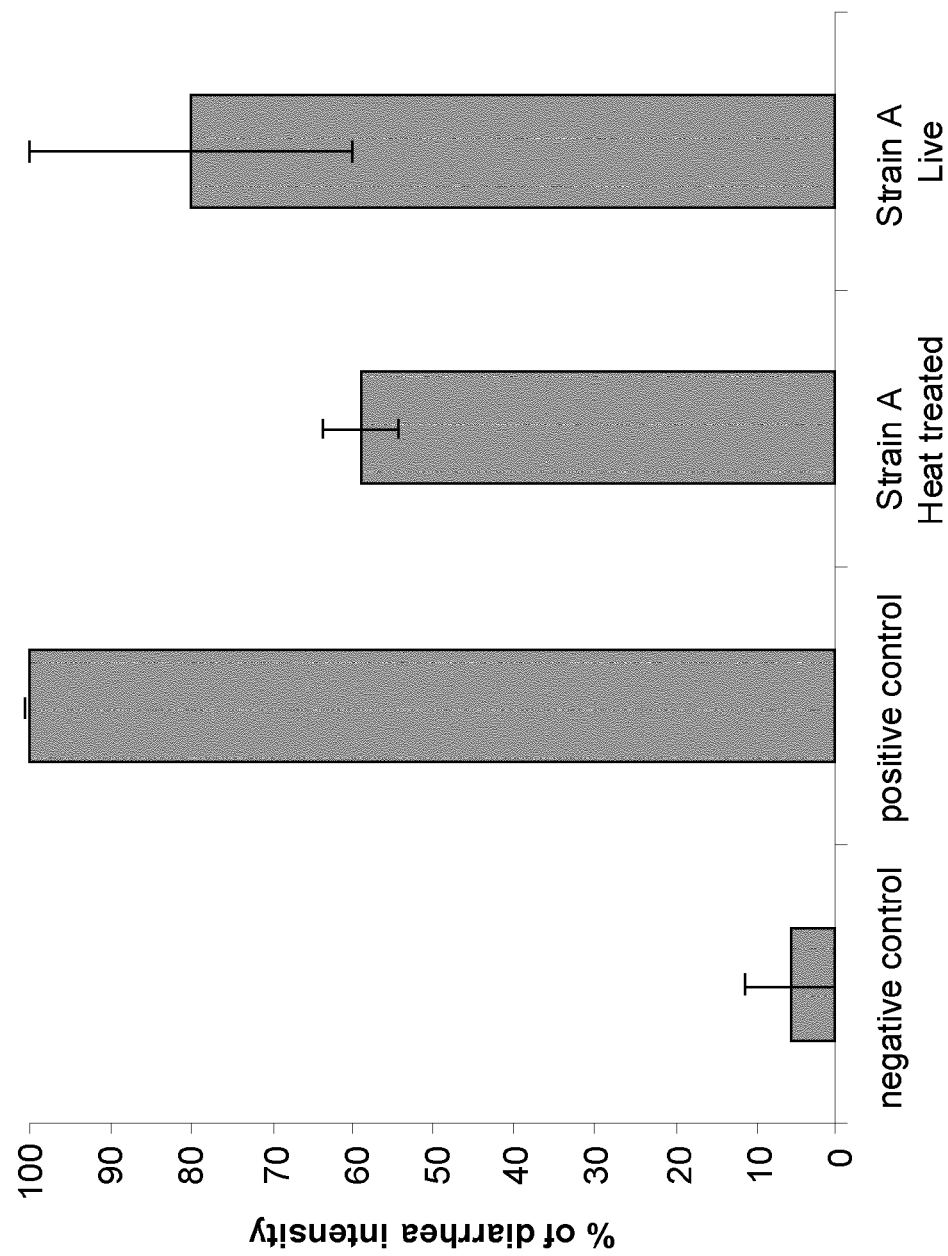
FIG. 9 shows the percentage of diarrhea intensity observed in OVA-sensitized mice challenged with saline (negative control), OVA-sensitized mice challenged with OVA (positive control) and OVA-sensitized mice challenged with OVA and treated with heat-treated or live *Bifidobacterium breve*

As compared to the positive control group, the intensity of diarrhea was significantly and consistently decreased after treatment with heat treated *B. breve* NCC2950 (41.1%±4.8) whereas the intensity of diarrhea was lowered by only 20±28.3% after treatment with live *B. breve* NCC2950. These results demonstrate that heat-treated *B. breve* NCC2950 exhibits an enhanced protective effect against allergic diarrhea than its live counterpart (FIG. 9).

As a consequence, the ability of probiotics to enhance the immune defences was shown to be improved after heat treatment.

EXAMPLE 3

The following frozen yoghurt composition may be prepared using standard freezing or low temperature extrusion techniques known in the art:

| Ingredient | g/100 g |
|---|---|
| Fat | 4.68 |
| Non-fat solids | 11.57 |
| Total solids | 38.53 |
| Carbohydrates | 28 |
| Added sugar | 22 |
| protein | 4.8 |
| Short term heat treated *Lactobacillus johnsonii* La1 | $10^8$ cfu |

EXAMPLES 4 AND 5

Materials and Methods

Bacterial Preparations:

Powders of *L. rhamnosus* NCC 4007 (CGMCC 1.3724, LPR), *L. paracasei* NCC 2461 (CNCM I-2116, ST11), *B. lactis* NCC 2818 (CNCM I-3446, BL818), *L. johnsonii* NCC 533 (CNCM I-1225, La1) and *B. longum* NCC 3001 (ATCC BA-999, BL999) were re-suspended in phosphate buffer saline (PBS, Sigma) in order to reach a final TS of 35% or a final wet solution containing around $5 \times 10^9$ cfu/ml.

Extrusion Recipes:

Dry mix of rice starch, corn semolina, calcium hydrogen phosphate, calcium carbonate, maltodextrin and milk powder was prepared according to the recipes presented in Tables 1 and 2. All the ingredients were mixed during 30 minutes using a batch mixer [Prodima's mixer, AC-MS (Prodima, St-Sulpice, Switzerland).

TABLE 1

Dry mix recipe used for extrusion (W/W percentage), Example 4

| Ingredients | (Weight in %) |
|---|---|
| Rice starch | 16.0 |
| Corn Semolina | 49.0 |
| Calcium Hydrogen Phosphate | 0.2 |
| Calcium Carbonate | 0.8 |
| Maltodextrin | 17.0 |
| Milk powder | 17.0 |

TABLE 2

Dry mix recipe used for extrusion (W/W percentage), Example 5

| Ingredients | (Weight in %) |
|---|---|
| Rice starch | 8.3 |
| Rice flour | 11.7 |
| Wheat flour | 20.0 |
| Corn Semolina | 58.8 |
| Calcium Hydrogen Phosphate | 1.0 |
| Calcium Carbonate | 0.2 |

Extrusion:

Experiments were performed using a co-rotating twin-screw extruder (Evolum BC25, Clextral, Firminy, FR) according to the flow chart (FIG. 10). Extrusion temperatures were controlled with six heated sections to reach product temperatures as high as 85, 100, 110, 120, 130, 140 and 160° C. Six barrels were used for the experiments, from n° 1 (feed zone) to n° 6 (before the die channel). Two different kinds of screw elements were used in the axis profile: C2F and C1F. A circular die of 3 mm was used to form extruded tubes. The dry mix was introduced into the extruder feed barrel at a flow rate of 10-12.0 kg/h using a feeder K-Tron (K-Tron, Lenzburg, CH). The bacterial preparation (described above) was injected into the extruder barrel n° 2 using a pump at a flow rate of 0.69-0.87 g/h. Water was injected into the extruder barrel n° 2 at a flow rate of 20-60 mL/min according to the heating temperature. Screw speed was set at 500 rpm. The resulting pressure was between 55 and 125 bars at the die channel. Extruded products containing bacteria were cut by hand and recovered on a stainless steel tray and then conditioned in aluminium bags. Reference control samples were extruded at 85° C., 100° C., 110° C., 120° C., 130° C., 140 or 160° C. in the same conditions without bacteria for analytical needs (hereafter 'extruded control').

An alternative process is shown in FIG. 12 in which probiotics are added into the dry mix recipe (Example 1, Table 1).

Cold Extrusion

Experiments were performed using a co-rotating twin-screw extruder (Evolum BC25, Clextral, Firminy, FR) according the flow chart (FIG. 11). Extrusion temperatures were controlled with six cooled sections to reach product temperatures between 25 and 40° C. Six barrels were used for the experiments, from n° 1 (feed zone) to n° 6 (before the die channel). Two different kinds of screw elements were used in the axis profile: C2F and C1F. A circular die of 3 mm was used to form extruded tubes. The dry mix was introduced into the extruder feed barrel at a flow rate of 8.0 kg/h using a feeder K-Tron (K-Tron, Lenzburg, CH). The bacterial preparation (described above) was injected into the extruder barrel n° 3 using a pump at a flow rate of 2 kg/h. Screw speed was set at 200, 500, 800, 1000 and 1200 rpm. The resulting pressure was between 1 and 70 bars at the die channel. Extruded products containing bacteria were cut by hand and recovered on a stainless steel tray and then conditioned in aluminium bags. Reference control samples were extruded at at 200, 500, 800, 1000 and 1200 rpm in the same conditions without bacteria for analytical needs (hereafter 'extruded control').

Extraction of Bacteria from the Extruded Product:

For Microscopy:

Bacteria were extracted from extruded samples as follows: 25 g of extruded samples were weighed and mixed with 225 ml of trypton salt and antifoam (Sigma). The mix was then mechanically disrupted by stomacher for 90 seconds and incubated at 68° C. for 15 minutes. Two successive filtration steps were then performed through 40 µm and 5 µm filters, respectively. Extruded products not containing probiotics, i.e. "extruded controls" or "controls", were submitted to the same protocol. The filtrated samples, hereafter called "extruded probiotics", were kept at 4° C. until use.

—For Human PBMC Cytokine Profiling:

Bacteria were extracted from extruded samples as follows: 10 g of extruded samples were weighed and mixed with 90 ml of PBS (Sigma). The mix was then mechanically disrupted by stomacher for 90 seconds. One filtration step was then performed through a 40 µm filter. Extruded products not containing probiotics, i.e. "extruded controls" or "controls", were submitted to the same protocol and were used as controls in the in vitro assays. The filtrated samples, hereafter called "extruded probiotics", were kept at −20° C. until use.

Bacterial Extraction from Cold Extruded Samples:

Bacteria were extracted from extruded samples as follows: 2 g of extruded samples were weighed and mixed with 18 ml of PBS. The mix was then homogenized for several seconds. Extruded products not containing probiotics, i.e. "extruded controls" or "controls", were submitted to the same protocol and were used as controls in the in vitro assays. The samples, hereafter called "extruded probiotics", were kept at −20° C. until use (human PBMC cytokine immunoprofiling).

Isolation of human PBMC:

Human peripheral blood mononuclear cells (PBMCs) were isolated from buffycoat from the transfusion center of the CHUV (Lausanne). The cells were diluted 1:2 with Hanks balanced salt solution (HBSS) (Sigma, Lachen, Switzerland). After a Histopaque gradient centrifugation (Sigma), separation by cell density gradient, mononuclear cells were collected at the interface and washed twice with HBSS. Cells were then resuspended in Iscove's Modified Dulbecco's Medium (IMDM, Sigma) supplemented with 10% foetal calf serum (Bioconcept, Paris, France), 1% L-glutamine (Sigma), 1% penicillin/streptomycin (Sigma) and 0.1% gentamycin (Sigma). PBMCs ($7 \times 10^5$ cells/well) were then incubated with different doses of extruded probiotics (doses stated in figures) in 48 well plates for 36 h. The effects of extruded probiotics and extruded controls were assessed on PBMCs from 8 individual donors splitted into two separate experiments. After 36 h incubation, culture plates were frozen and kept at −20° C. until cytokine measurement.

Cytokine Measurements:

Levels of cytokines (IL-12p40, TNF-$\alpha$ and IL-10) in cell culture supernatants after 36 h incubation were determined by electrochemiluminescence based multiplex (MesoScale Discovery, Gaithersburg, Md.) following the manufacturer's instructions. IL-12p40 and TNF-$\alpha$ are pro-inflammatory cytokines, whereas IL-10 is a potent anti-inflammatory and regulatory mediator. Results are expressed as means (pg/ml)+/−SEM of 4 individual donors and are representative of two individual experiments performed with 4 donors each.

PCA Analysis

Numerical cytokine values (pg/ml) determined by multiplex (see above) for each strain were transferred into BioNumerics v5.10 software (Applied Maths, Sint-Martens-Latem, Belgium). A Principal Component Analysis (PCA, dimensioning technique) was performed on this set of data. Substraction of the averages over the characters and division by the variances over the characters were included in this analysis. Strains inducing high levels of pro-inflammatory cytokines cluster in the right side of the graph, as opposed to strains inducing low amounts of pro-inflammatory cytokines that cluster in the left side panel.

Optical Microscopy

Bacteria were extracted from extruded samples as previously described in the section "Extraction of bacteria from the extruded product" with some changes. Samples were submitted to enzymatic digestion by alpha-amylase for 1 hour at 68° C. prior to filtration step followed by optical microscopic observations (magnification 40× and 100×).

For PCR Analyses:

DNA Extraction of Extruded Bacteria for PCR:

DNA was extracted from extruded samples using the QIAquick and QIAamp (Qiagen) kit following the supplier instruction with the following modification. 2 g of extruded samples were weighed and mixed with 10 ml of CTAB (Hexadecyltrimethyl-ammonium bromide) (AppliChem) and 225 ul of protease (Qiagen) to obtain a final concentration of 450 µg/ml. Then the mix was incubated in a water bath for 1 hour at 65° C. The preparation was centrifuged and the aqueous phase was collected and mixed with an equal volume of chloroform (Merck). After centrifugation, the supernatant was transferred with 5 volumes of PB Buffer (Qiagen) on a QIAamp Maxi column, attached to a vacuum pump at a maximum of −600 mbar. The column was washed twice with PE buffer (Qiagen) and dried by centrifugation. The purified DNA was eluted with 1 ml of EB buffer (Qiagen) for 5 minutes and recovered after centrifugation. A second purification was done as previously using the eluted DNA with a QIAquick column (Qiagen).

Polymerase Chain Reaction (PCR)

PCR were carried out in a Thermocycler (GeneAmp PCR System 9700, Applied Biosystem). 1 μl of DNA purified were added in 24 μl of amplification mixture. Amplification were carried out in 0.2 ml Thermo-Strip tubes containing the reaction buffer: each dATP, dCTP, dGTP, dTTP nucleotide (Roche Applied Science) at 2.5 mM, 10 pmol/μl of each specific primer, 2.5 μl of 10×PCR buffer containing 15 mM MgC12 (Applied Biosystem), 1.25 units of AmpliTaq Gold (Applied Biosystem), and Nuclease free water. 30 cycles of amplification were performed, each cycle consisting of denaturation step (30 sec at 94° C.) followed by an annealing step of 30 seconds at (60° C.) and an elongation step (30 sec at 72° C.). The elongation step was extended to 7 minutes at 72° C. during the last cycle. The PCR products were then analysed by agarose gel electrophoresis or by Automated Electrophorectic Separations (LabChip GXII, Caliper)

Electrophoresis:

PCR products were visualized on agarose gel.

10 μl of the PCR product were mixed with 2 μl of blue loading buffer and loaded on a 1.2% agarose gel containing 1×SYBR Safe. Samples and a molecular weight ladder were run for 1 hour at 80V. Pictures of the gel were taken with UV illumination.

Automated Electrophoretic Separation of DNA:

DNA chip was prepared by adding Gel-Dye and DNA marker (Caliper). PCR products were transferred into a 96 well plate and loaded in the LabChip GXII. Samples were detected by laser-induced fluorescence and data were automatically analyzed with System software providing the size (pb) and the quantity (ng/μl) of the product. Results were reported as virtual gel.

Results

The immune profiles of extruded samples of *B. longum* NCC3001 were assessed in vitro using the PBMC assay. Pro-inflammatory (TNF-α and IL-12p40) and anti-inflammatory (IL-10) cytokines were measured in cell culture supernatants after 36 h incubation. Control extruded products without bacterial supplementation induced low levels of pro- and anti-inflammatory cytokines. Inclusion of live *B. longum* NCC3001 in the extrusion process (temperature of 130° C.) dramatically stimulated the production of cytokines in a dose dependent manner. The best cytokine induction was found at a dose of about $10^8$ equivalent cfu/ml.

We then addressed the question whether extrusion at different temperatures (110° C. and 120° C.) would lead to similar in vitro immune activation. We therefore compared the samples resulting from extrusion at three different temperatures at the dose of $10^9$ equivalent cfu/g. All extruded samples containing *B. longum* NCC3001 efficiently activated immune blood cells, as compared to the control. Temperatures applied during the extrusion did not seem to impact on the immune profiles of extruded *B. longum* samples since relatively high levels of cytokines were induced at each temperature tested. *B. longum* NCC3001 was added as live bacteria ($10^{10}$ cfu/mL) into the extruder as shown in FIG. 1. We checked the residual viable counts at the end of the process by plating samples on MRS+Cysteine agar. All the added bacteria were rendered non replicating by the process since no colonies were observed in any samples extruded at 110° C., 120° C. and 130° C. (data not shown). The presence of rod shaped bacteria in extruded *B. longum* NCC3001 containing products (magnitude 100×) as opposed to the control sample, allowed us to conclude that the in vitro immune response previously described with extruded *B. longum* NCC3001 samples is therefore due to the presence of non viable bacteria in the final products.

We then addressed the question whether extrusion of different strains, at different temperatures (from 85° C. to 140° C.) and at different screw speeds (from 200 rpm to 1200 rpm) would lead to similar in vitro immune activation. We therefore compared the samples resulting from extrusion of 4 additional strains at five different temperatures and five different screw speeds at the dose of $10^9$ equivalent cfu/g. As illustrated in FIG. 13 extruded samples containing non replicating *L. paracasei* NCC2461 (ST11), and *B. lactis* NCC2818 (BL818) and *L. johnsonii* NCC533 efficiently activated immune blood cells, as compared to the controls. These data are in agreement with the data previously found for *B. longum* NCC3001. Temperatures applied during the extrusion—i.e hot or cold extrusion—did not seem to impact on the immune profiles of extruded *B. longum* samples since relatively high levels of cytokines were induced at each temperature tested. Likewise, screw speeds above 600 rpm allowed generating non replicating strains (no cfu detectable by plating) that were still triggering the immune cells (FIGS. 14 and 15). So mechanical shearing, independently of temperature, can be used to render probiotics non replicating while maintaining their capacity to stimulate immune cells.

PCA analyses revealed that extruded bacteria triggered immune cell activation in vitro (FIGS. 14 and 15). However, extruded and live bacteria were found in separate clusters, indicating that the extruded bacteria are able to exhibit improved or newly acquired immune properties, as compared to live controls.

Rod shapes were detected by microscopy in all samples extruded with the different probiotic strains, but not in their respective controls. The presence of the probiotic strains in extruded samples was validated by PCR analysis using strain specific probes. For example, chromosomal DNA of *L. paracasei* NCC2461, *B. longum* NCC3001, *B. lactis* NCC2818 and *L. johnsonii* NCC533 was detected, as shown by specific bands on virtual gel or on agarose gel.

Probiotic bacteria were added as live bacteria ($10^{10}$ cfu/mL) into the extruder in FIGS. 10 and 12. We checked the residual viable counts at the end of the process by plating samples on MRS+/−Cysteine agar. All the added bacteria were rendered non replicating by the process since no colonies were observed in any samples extruded at temperatures from 85° C. to 160° C. and 140° C. and cold extruded at a screw speed from 800 rpm to 1200 rpm (data not shown). The presence of rod shaped bacteria in extruded products (magnitude 100×) as opposed to the control samples, allowed us to conclude that the in vitro immune activation observed in response to extruded products is therefore due to the presence of non viable bacteria in the final products.

As a result, we showed that extrusion of raw materials with live probiotic bacteria at different temperatures and shearing conditions led to extruded products containing non replicating probiotic microorganisms with immune stimulating activities. To our best knowledge, the process of extrusion has never been reported for generation of non viable non-replicating probiotics that are still able to activate the immune system. The concept can be generalized to any probiotic bacterium or dairy starters and any extrusion temperatures or conditions. This invention thus describes a novel way of generating non replicating probiotics that deliver health beneficial properties and leads to new concepts of extruded products. In particular, the present invention also describes a novel way of generating non replicating probiotics that exhibit improved or newly acquired immune stimulating activities.

The invention claimed is:

1. A frozen yoghurt composition comprising about $10^6$ to $10^{12}$ cfu of non-replicating probiotic micro-organisms per serving, whereby the non-replicating probiotic micro-organisms are rendered non-replicating by a heat treatment at a temperature from 120 to 140° C., wherein the non-replicating probiotic micro-organisms are selected from the group consisting of Bifidobacterium longum NCC 3001, Bifidobacterium longum NCC 2705, Bifidobacterium breve NCC 2950, Bifidobacterium lactis NCC 2818, Lactobacillus johnsonii La1, Lactobacillus paracasei NCC 2461, Lactobacillus rhamnosus NCC 4007, Lactobacillus reuteri DSM17938, Lactobacillus reuteri ATCC55730, Streptococcus thermophilus NCC 2019, Streptococcus themophilus NCC 2059, Lactobacillus casei NCC 4006, Lactobacillus acidophilus NCC 3009, Lactobacillus casei ACA-DC 6002(NCC 1825), Escherichia coli Nissle, Lactobacillus bulgaricus NCC 15, Lactococcus lactis NCC 2287, and combinations thereof.

2. The frozen yoghurt composition in accordance with claim 1 comprising about 0-12 weight-% fat, about 5-15 weight-% non fat milk solids, about 5-32 weight-% carbohydrates, about 1-5 weight-% proteins and a total solid content of about 30-45 weight-%.

3. The frozen yoghurt composition in accordance with claim 1, comprising about 1-25 weight-% sugar.

4. The frozen yoghurt composition in accordance with claim 1, comprising an edible support associated with the frozen yoghurt, the support being edible by humans and comprising prebiotics.

5. The frozen yoghurt composition in accordance with claim 1 comprising prebiotics.

6. The frozen yoghurt composition in accordance with claim 4, wherein the edible support comprises about 0.1% to about 10% of prebiotics selected from the group consisting of vegetable pectins; chito-, fructo-, gentio-, galacto-, isomalto-, manno- and xylo-oligosaccharides; soya bean, Polymnia sonchifolia, artichoke, oat, onion and asparagus oligosaccharides; and combinations thereof.

7. The frozen yoghurt composition in accordance with claim 1, wherein the heat treatment is performed for 1-30 seconds.

8. The frozen yoghurt composition in accordance with claim 1, wherein the heat treatment is performed for 1-120 seconds.

9. A method for the treatment of inflammatory disorders comprising the step of administering to an individual having an inflammatory disorder a frozen yoghurt composition comprising 0.005 mg-1000 mg of non-replicating probiotic micro-organisms per daily dose, whereby the non-replicating probiotic micro-organisms are rendered non-replicating by a heat treatment at a temperature from 120 to 140° C., wherein the non-replicating probiotic micro-organisms are selected from the group consisting of Bifidobacterium longum NCC 3001, Bifidobacterium longum NCC 2705, Bifidobacterium breve NCC 2950, Bifidobacterium lactis NCC 2818, Lactobacillus johnsonii La1, Lactobacillus paracasei NCC 2461, Lactobacillus rhamnosus NCC 4007, Lactobacillus reuteri DSM17938, Lactobacillus reuteri ATCC55730, Streptococcus thermophilus NCC 2019, Streptococcus thermophilus NCC 2059, Lactobacillus casei NCC 4006, Lactobacillus acidophilus NCC 3009, Lactobacillus casei ACA-DC 6002 (NCC 1825), Escherichia coli Nissle, Lactobacillus bulgaricus NCC 15, Lactococcus lactis NCC 2287, and combinations thereof.

10. The frozen yoghurt composition in accordance with claim 1, wherein the heat treatment is performed for 5-15 seconds.

11. A method for the treatment of disorders related to a compromised immune defense comprising the step of administering to an individual having a disorder related to a compromised immune defense a frozen yoghurt composition comprising 0.005 mg-1000 mg of non-replicating probiotic micro-organisms per daily dose, whereby the non-replicating probiotic micro-organisms are rendered non-replicating by a heat treatment at a temperature from 120 to 140° C., wherein the non-replicating probiotic micro-organisms are selected from the group consisting of Bifidobacterium longum NCC 3001, Bifidobacterium longum NCC 2705, Bifidobacterium breve NCC 2950, Bifidobacterium lactis NCC 2818, Lactobacillus johnsonii La1, Lactobacillus paracasei NCC 2461, Lactobacillus rhamnosus NCC 4007, Lactobacillus reuteri DSM17938, Lactobacillus reuteri ATCC55730, Streptococcus thermophilus NCC 2019, Streptococcus thermophilus NCC 2059, Lactobacillus casei NCC 4006, Lactobacillus acidophilus NCC 3009, Lactobacillus casei ACA-DC 6002 (NCC 1825), Escherichia coli Nissle, Lactobacillus bulgaricus NCC 15, Lactococcus lactis NCC 2287, and combinations thereof.

12. The frozen yoghurt composition in accordance with claim 1 comprising probiotics, wherein at least 90% of the probiotics are the non-replicating probiotic micro-organisms.

13. The frozen yoghurt composition in accordance with claim 1 wherein the non-replicating probiotic micro-organisms comprise Lactobacillus paracasei NCC 2461.

14. The frozen yoghurt composition in accordance with claim 1 wherein the non-replicating probiotic micro-organisms comprise Lactobacillus rhamnosus NCC 4007.

15. The frozen yoghurt composition in accordance with claim 1 containing $10^4$ to $10^9$ cfu of the non-replicating micro-organisms per gram of dry composition.

* * * * *